(12) United States Patent
Liu et al.

(10) Patent No.: US 11,733,198 B2
(45) Date of Patent: Aug. 22, 2023

(54) METHOD FOR DETERMINING ANALYTE CONCENTRATION IN A SAMPLE

(71) Applicant: Lifescan IP Holdings, LLC, Malvern, PA (US)

(72) Inventors: Zuifang Liu, Inverness (GB); David McColl, Inverness (GB); Robert Donald, Inverness (GB); Anna Salgado, Inverness (GB); Antony Smith, Inverness (GB)

(73) Assignee: LIFESCAN IP HOLDINGS, LLC, Malvern, PA (US)

( * ) Notice: Subject to any disclaimer, the term of this patent is extended or adjusted under 35 U.S.C. 154(b) by 117 days.

(21) Appl. No.: 17/346,765

(22) Filed: Jun. 14, 2021

(65) Prior Publication Data

US 2021/0381998 A1 Dec. 9, 2021

Related U.S. Application Data

(62) Division of application No. 16/021,403, filed on Jun. 28, 2018, now Pat. No. 11,035,819.

(51) Int. Cl.
*G01N 27/327* (2006.01)
*A61B 5/145* (2006.01)
(Continued)

(52) U.S. Cl.
CPC ..... *G01N 27/3274* (2013.01); *G01N 27/3273* (2013.01); *A61B 5/14532* (2013.01);
(Continued)

(58) Field of Classification Search
CPC .. G01N 27/327; G01N 27/3272; G01N 27/48; G01N 27/26; G01N 27/10;
(Continued)

(56) References Cited

U.S. PATENT DOCUMENTS

| 7,160,251 B2 | 1/2007 | Neel et al. |
| 8,603,768 B2 | 12/2013 | Chatelier et al. |

(Continued)

FOREIGN PATENT DOCUMENTS

| GB | 2531728 A | 5/2016 |
| WO | 2012012341 | 1/2012 |
| WO | 2016066575 | 5/2016 |

OTHER PUBLICATIONS

Federal Service for Intellectual Property (FIIP); Search Report; Application No. 2022103985/28 (008383); Application Filing Date: Jul. 24, 2019; 4 pages.

(Continued)

*Primary Examiner* — Gurpreet Kaur
(74) *Attorney, Agent, or Firm* — Barclay Damon LLP

(57) ABSTRACT

A method for determining a concentration of an analyte in a fluidic sample is described. A sample is applied to a biosensor including an electrochemical cell having electrodes. A predetermined voltage waveform is applied during at least first and second time intervals. At least first and second current values are measured during the first and second time intervals, respectively. A turning point time is determined during the first time interval at which the measured first current values transition from a first to a second profile. The concentration of analyte in the sample is calculated based on determined turning point time and at least one measured current value. In another example, a physical characteristic of the sample is estimated based on measured current values. The concentration is calculated using a first or second model if the estimated physical characteristic of the sample is in a first or second range, respectively.

14 Claims, 16 Drawing Sheets

(51) Int. Cl.
*G01N 27/48* (2006.01)
*G01N 27/416* (2006.01)

(52) U.S. Cl.
CPC .. *A61B 2562/0295* (2013.01); *G01N 27/3272* (2013.01); *G01N 27/3277* (2013.01); *G01N 27/4168* (2013.01); *G01N 27/48* (2013.01)

(58) Field of Classification Search
CPC ........... G01N 27/3274; G01N 27/3277; G01N 27/3273; A61B 5/1468; A61B 5/14532; A61B 5/157; A61B 2562/0295
See application file for complete search history.

(56) References Cited

U.S. PATENT DOCUMENTS

| | | | |
|---|---|---|---|
| 8,709,232 B2 | 4/2014 | Matzinger | |
| 2009/0301899 A1 | 12/2009 | Hodges | G01N 27/3274 205/777.5 |
| 2014/0134655 A1 | 5/2014 | Elder | G01N 27/3274 435/14 |
| 2017/0241940 A1* | 8/2017 | Liu | G01N 27/48 |
| 2018/0306744 A1 | 10/2018 | Malecha et al. | |

OTHER PUBLICATIONS

Federal Service for Intellectual Property (FIIP); Official Action of Substantive Examination; Application No. 2022103985/28(008383); Application Filing Date: Jul. 24, 2019; 12 pages.

* cited by examiner

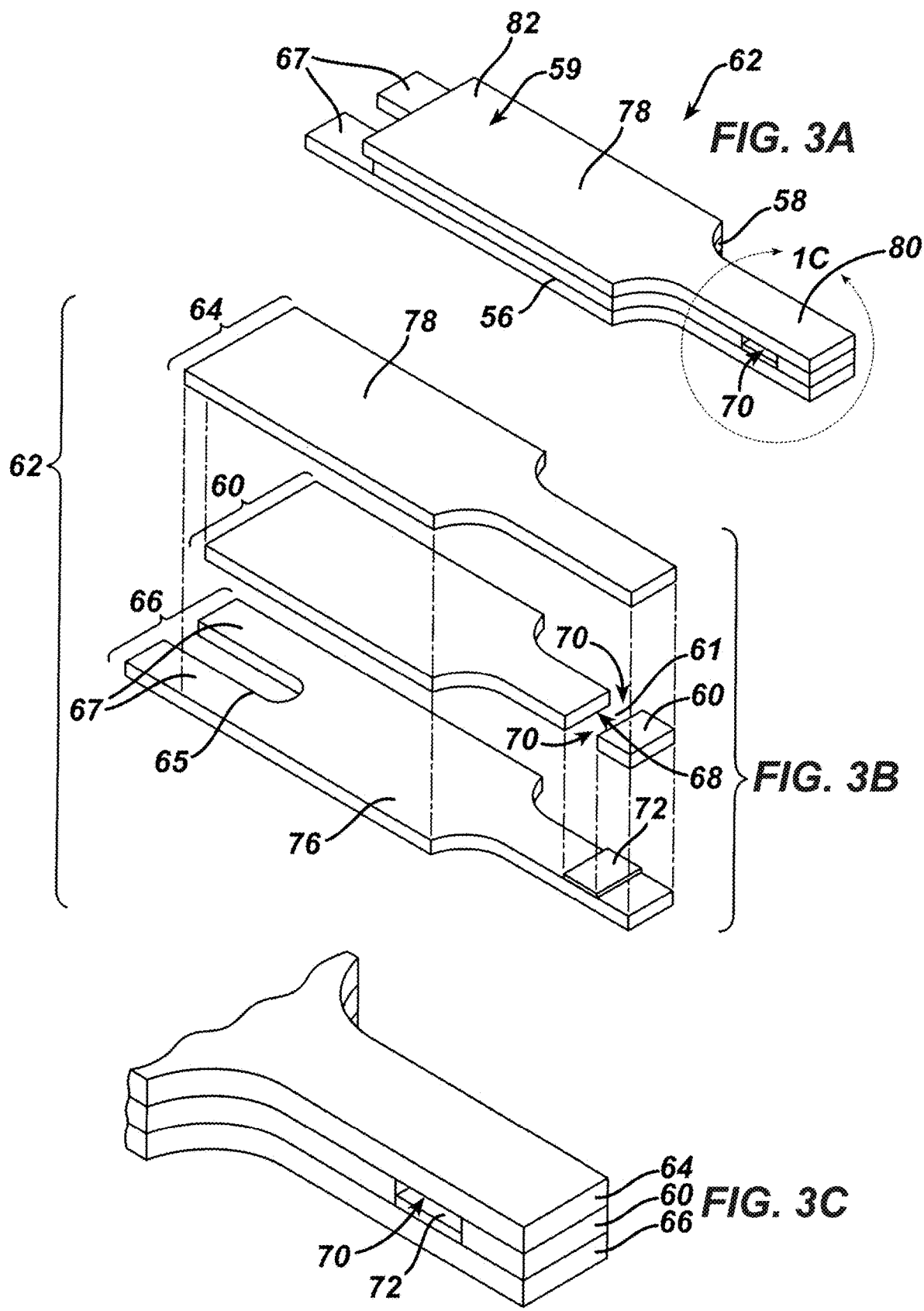

METHOD FOR DETERMINING ANALYTE CONCENTRATION IN A SAMPLE

CROSS REFERENCE TO RELATED APPLICATION

This application is a divisional application of U.S. application Ser. No. 16/021,403, filed Jun. 28, 2018, the entire contents of which are herein incorporated by reference.

TECHNICAL FIELD

This application is generally directed to analyte measurement systems, and more specifically to methods for determining the concentration of an analyte in a sample such as blood glucose, in which the analyte includes a physical characteristic or property that changes the concentration measurement inappropriately, such as an interferent factor, e.g., hematocrit, uric acid or another interferent.

BACKGROUND

Analyte detection in physiological fluids, e.g., blood or blood derived products, is of ever increasing importance to today's society. Analyte detection assays find use in a variety of applications, including clinical laboratory testing, home testing, etc., where the results of such testing play a prominent role in periodic diagnosis and management in a variety of disease conditions. Analytes of interest include glucose for diabetes management and cholesterol, among others. In response to the growing importance of analyte detection, a variety of testing protocols and devices for both clinical and home use have been developed.

One method that is employed for analyte detection of a liquid sample is the electrochemical method. In such a method, an aqueous liquid sample such as a blood sample is deposited onto a biosensor and filled into a sample-receiving chamber of an electrochemical cell that includes two electrodes, e.g., a counter electrode and working electrode. The analyte is allowed to react with a redox reagent to form an oxidizable (or reducible) substance in an amount corresponding to the analyte concentration. The quantity of the oxidizable (or reducible) substance present is then estimated electrochemically and related to the amount of analyte present in the deposited sample.

However, any analyte measurement system may be susceptible to various modes of inefficiency and/or error. For example, interferents present in the physiological fluid may lead to inaccurate analyte measurements. As one particular example, the presence of uric acid in blood can interfere with the glucose measurements, leading to erroneous results. In some cases, these erroneous results could potentially mislead a subject into administering the wrong dosage of medicine with potentially catastrophic results. Therefore, an ever existing need exists for improvements in the accuracy of analyte concentration measurements taken in the presence of interferents in a physiological fluid sample.

BRIEF DESCRIPTION OF THE DRAWINGS

So that the manner in which the features of the disclosure can be understood, a Detailed Description may be had by reference to certain embodiments, some of which are illustrated in the accompanying drawings. It is to be noted, however, that the drawings illustrate only certain embodiments and are therefore not to be considered limiting of its scope, for the scope of the disclosed subject matter encompasses other embodiments as well. The drawings are not necessarily to scale, emphasis generally being placed upon illustrating the features of certain embodiments. In the drawings, like numerals are used to indicate like parts throughout the various views.

FIG. 3A is a perspective view of an assembled test strip suitable for use in the analyte measurement system of FIGS. 1 and 2;

FIG. 3B is an exploded perspective view of the test strip of FIG. 3A;

FIG. 3C is an expanded perspective view of a proximal portion of the test strip of FIGS. 3A and 3B;

DETAILED DESCRIPTION

Figure 1:
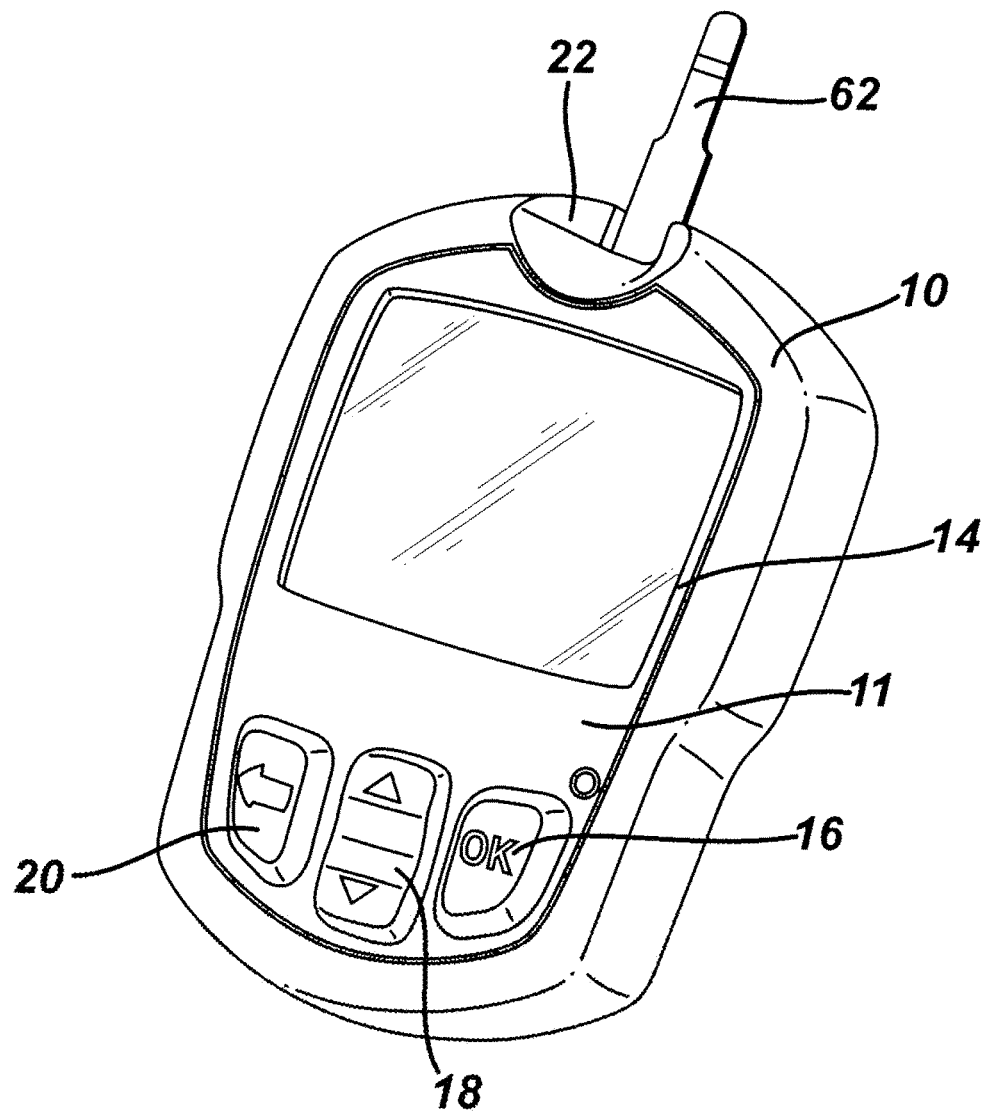
FIG. 1 illustrates a perspective view of an analyte measurement system including a test meter and biosensor (test strip), in accordance with aspects set forth herein.

The following Detailed Description should be read with reference to the drawings, in which like elements in different drawings are identically numbered. The drawings, which are not necessarily to scale, depict selected embodiments and are not intended to limit the scope of the invention. The Detailed Description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient," "host," "user," and "subject" refer to any human or animal subject and are not intended to limit the systems or methods to human use, although use of the subject techniques in a human patient represents a preferred embodiment.

The present disclosure relates, in part, to techniques for determining concentration of an analyte, with a biosensor such as a disposable test strip. A biased measurement (e.g., higher than actual) could lead to an incorrectly high dose of insulin being administered to a patient, resulting in a severe impact on the health of the patient. Testing has shown that analytes having certain interferents, e.g., uric acid or ascorbic acid present in a sample, may undergo oxidation and thus change the current response as compared to a sample with less interferents. In attempts to find ways to improve the accuracy of blood glucose measurements, a technique is herein provided to more accurately account for the interferent, including enhanced measurement techniques and/or correction for physical characteristic measurements that are influenced by the interferents. Consequently, various aspects of a method for determining analyte concentration in a sample are presented herein. In one example of the present technique, a measurement technique is applied to the sample, and the analyte concentration is determined by correcting for the presence of the interferent. In another example, an estimated physical characteristic is computed, and then one of many different linear models are chosen to calculate the analyte concentration based on the physical characteristic and other parameters.

Generally stated and according to at least one embodiment, a method is provided for determining a concentration of an analyte in a fluidic sample. A sample is applied to a biosensor that includes an electrochemical cell having electrodes. A predetermined voltage waveform is applied during at least first and second time intervals. At least first and second current values are measured during the first and second time intervals, respectively. A turning point time is determined during the first time interval at which the measured first current values transition from a first to a second profile. The concentration of the analyte in the sample is calculated based on the determined turning point time and at least one measured current value.

In one embodiment, the calculating step is based on the determined turning point time and at least one current value of the measured first current values and at least one current value of the measured second current values. In another embodiment, the calculating step is based on a turning point current value at the turning point time.

In one specific implementation, calculating the analyte concentration includes using an equation of the form $G_{basic} = \sum_{i=1}^{m} \sum_{j=0}^{m} a_{i,j} x_i x_j + c$, in which:

$G_{basic}$ is the analyte concentration (in mg/dL);

$a_{i,j}$ are coefficients;

$x_0$ is a constant (e.g., equal to 1);

$x_1$ is $t_{Turn}$, the turning point time (in seconds);

$x_2$ is $i_r$, a sum of at least some of the measured second current values of the second time interval (in microamperes);

$x_3$ is one of the first current values in the first time interval (in microamperes);

$x_4$ is $i_{Turn}$, a current value at $t_{Turn}$ (in microamperes);

$x_5$ is the inverse of one of the first current values in the first time interval (in 1/microamperes);

$x_6$ is the inverse of one of the first current values in the first time interval (in 1/microamperes); and c is a predetermined constant.

In another specific implementation, the predetermined voltage waveform is further applied during a third time interval, in which the measuring step further comprises measuring third current values during the third time interval, and in which the calculating step is based on the determined turning point time and at least one current value of the measured first, second and third current values. In such a case, calculating the analyte concentration may include using an equation of the form $G_{basic} = \sum_{i=1}^{m} \sum_{j=0}^{m} a_{i,j} x_i x_j + c$, in which:

$G_{basic}$ is the analyte concentration (in mg/dL);

$a_{i,j}$ are predetermined coefficients;

$x_0$ is a constant (e.g., equal to 1);

$x_1$ is $t_{Turn}$, the turning point time (in seconds);

$x_2$ is $i_r$, a sum of at least some of the measured third current values of the third time interval (in microamperes);

$x_3$ is one of the second current values in the second time interval (in microamperes);

$x_4$ is $i_{pb}$, close to a peak of the second current values in the second time interval (in microamperes);

$x_5$ is the inverse of one of the first current values in the first time interval (in 1/microamperes);

$x_6$ is the inverse of one of the second current values in the second time interval (in 1/microamperes); and c is a predetermined constant.

Figure 5A:
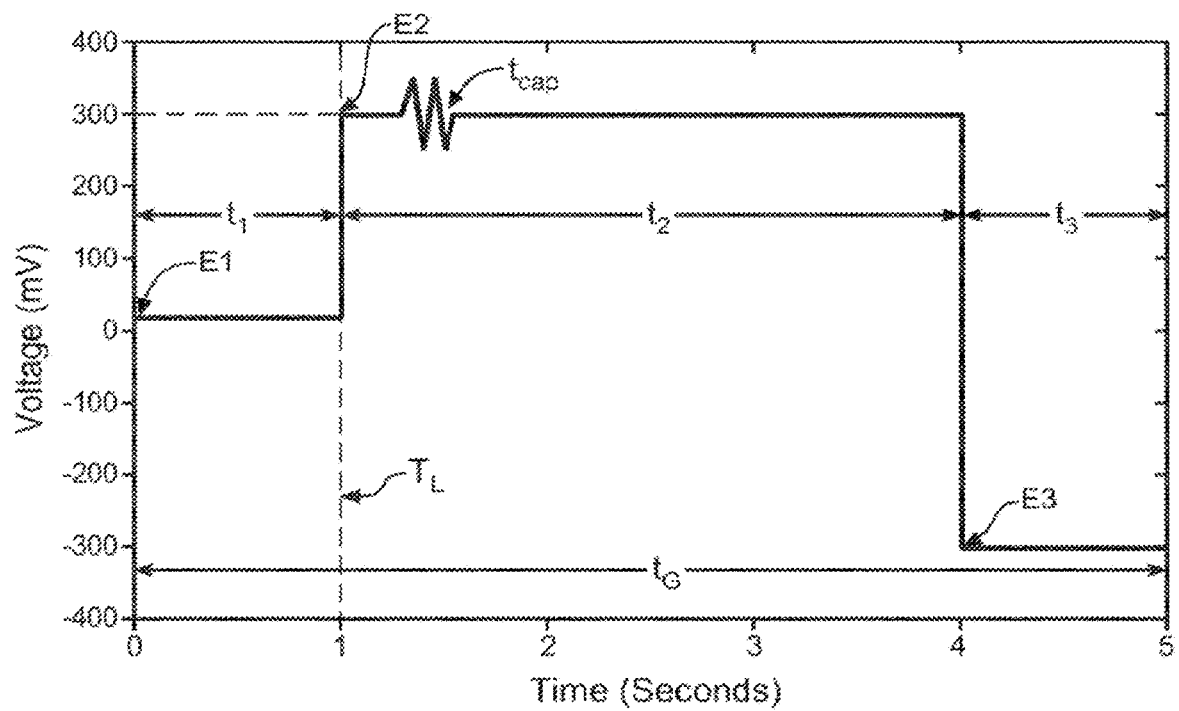
FIG. 5A shows an example of a test waveform applied by the test meter of FIG. 4 to the working and counter electrodes of a test strip for prescribed time intervals for the determination of an analyte in a sample applied to the test strip.
Figure 5B:
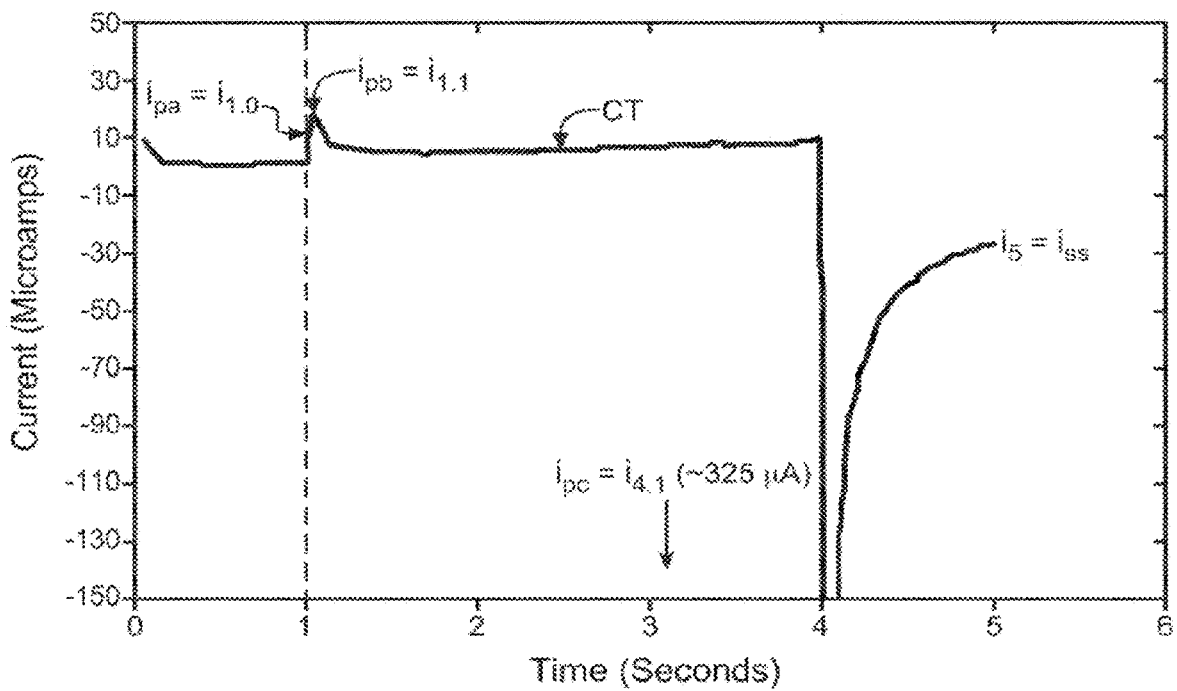
FIG. 5B depicts measured current over time based on the waveform of FIG. 5A for a nominal test strip.

In a further specific implementation using the waveform set forth in FIG. 5A and resulting current transient set forth in FIG. 5B, calculating the analyte concentration comprises using an equation of the form $G_{basic} = (t_{Turn})^p \cdot a \cdot |i_{2corr}| - z_{gr}$, in which:

$G_{basic}$ is the analyte concentration (in milligrams per deciliter);

$t_{Turn}$ is the turning point time (in seconds);

$$i_{2corr} = \frac{|i_{pc}| + b|i_{ss}| - c|i_{pb}|}{|i_{pc}| + b|i_{ss}|} \cdot i_r (\text{in microamperes});$$

$i_{pc}$ is a current close to the negative peak of the third current values in the third time interval (in microamperes);

$i_{pb}$ is a current close to the peak of the second current values in the second time interval (in microamperes);

$i_{ss}$ is a steady state of the third current values in the third time interval;

$i_r$ is a sum of at least some of the measured second current values of the third time interval (in microamperes); and a, b, p and $z_{gr}$ are predetermined coefficients.

In one example, the method further includes driving, after applying the sample to the biosensor, a triggering current between the electrodes of the electrochemical cell, measuring triggering voltage values during driving of the triggering current; and triggering the predetermined voltage waveform upon the measured triggering voltage dropping below a triggering threshold voltage.

In another example, the triggering current is between 500-700 nA and the triggering threshold voltage is between 800-1,100 mV.

After triggering the predetermined voltage waveform, the current values transition from a first profile to a second profile. The first profile can deviate from a Cottrell profile and the second profile essentially follows a Cottrell profile. In another aspect, an interferent undergoes oxidation at a bare electrode of the electrodes of the electrochemical cell. In a further aspect, the interferent comprises uric acid or ascorbic acid.

In one example, the electrodes of the electrochemical cell comprise a bare electrode and an at least partially reagent covered electrode. The electrodes of the electrochemical cell can be disposed co-facially or the electrodes can be co-planar. The measuring of the first and second current values is at a frequency between 50-200 Hz.

In another aspect, a sample is applied to a biosensor including an electrochemical cell having electrodes. A predetermined voltage waveform is applied during at least first and second time intervals. At least first and second current values are measured during the first and second time intervals, respectively. A turning point time is determined during the first time interval at which the measured first current values transition from a first to a second profile. A physical characteristic of the sample (e.g., hematocrit) is estimated based on the measured current values. The concentration is calculated using one of a number of specific models (e.g., first, second, third, etc., models) if the estimated physical characteristic of the sample is in a specific range (e.g., first, second, third, etc., ranges).

In one embodiment, the first model comprises first coefficients and the second model comprises second coefficients, in which the first coefficients and the second coefficients are determined by linear optimization. In another embodiment, estimating the physical characteristic comprises using the turning point time.

In one specific example, calculating the analyte concentration using the first model comprises using an equation of the form $G_{basic}^1 = \sum_{i=1}^{m} \sum_{j=0}^{m} a_{i,j}^1 x_i^1 x_j^1 + c_1$, and calculating the analyte concentration using the second model comprises using an equation of the form:

$$G_{basic}^2 = \sum_{i=1}^{m} \sum_{j=0}^{m} a_{i,j}^2 x_i^2 x_j^2 + c_2, \text{ in which:}$$

$G_{basic}^1$ is the analyte concentration calculated using the first model (in mg/dL);

$a_{i,j}^1$ are first model predetermined coefficients;

$x_0^{1,2}$ are constants (e.g., equal to 1);

$x_i^1$ are first model predictors based on the measured current values;

$c_1$ is a first model predetermined constant;

$G_{basic}^2$ is the analyte concentration calculated using the second model (in mg/dL);

$a_{i,j}^2$ are second model predetermined coefficients;

$x_i^1$ are second model predictors based on the measured current values; and $c_2$ is a second model predetermined constant.

The above embodiments are intended to be merely examples. It will be readily apparent from the following discussion that other embodiments are within the scope of the disclosed subject matter.

Specific working examples will now be described with respect to FIGS. 1-6H.

FIG. 1 illustrates a diabetes management system that includes a portable test meter 10 and a biosensor, the latter being provided in the form of a disposable test strip 62 that is configured for the detection of blood glucose. For purposes of the following discussion, the portable test meter 10 is synonymously referred to throughout as an analyte measurement and management unit, a glucose meter, a meter, and/or a meter unit. Though not shown in this view and in at least one embodiment, the portable test meter may be combined with an insulin delivery device, an additional analyte testing device, and a drug delivery device. The portable test meter 10 may be connected to a remote computer or remote server via a cable or a suitable wireless technology such as, for example, GSM, CDMA, Bluetooth, WiFi and the like. Such analyte measurement systems are described in U.S. Pat. No. 8,709,232 B2, issued Apr. 29, 2014, and entitled "Analyte Measurement Technique and System," and International Patent Publication No. WO 2012/012341 A1, published Jan. 26, 2012, and entitled "System and Method for Measuring an Analyte in a Sample," each of which is herein incorporated by reference in its entirety.

Still referring to FIG. 1, the portable test meter 10 is defined by a housing 11 having a plurality of user interface buttons (16, 18, and 20) that are disposed on a facing surface. A display 14 is provided in addition to a strip port opening 22 that is configured to receive a biosensor (test strip 62). The user interface buttons (16, 18, and 20) may be configured to allow the entry of data, navigation of menus, and execution of various commands. It will be readily apparent that the configuration and functionality of the user interface buttons 16, 18, 20 of the portable test meter 10 is intended to be an example and modifications and variations are possible. According to this specific embodiment, the user interface button 18 may be in the form of a two-way toggle switch. Data may include values representative of analyte concentration, and/or information, which are related to the everyday lifestyle of an individual. Information, which is related to the everyday lifestyle, may include food intake, medication use, occurrence of health check-ups, and general health condition and exercise levels of an individual.

Figure 2:
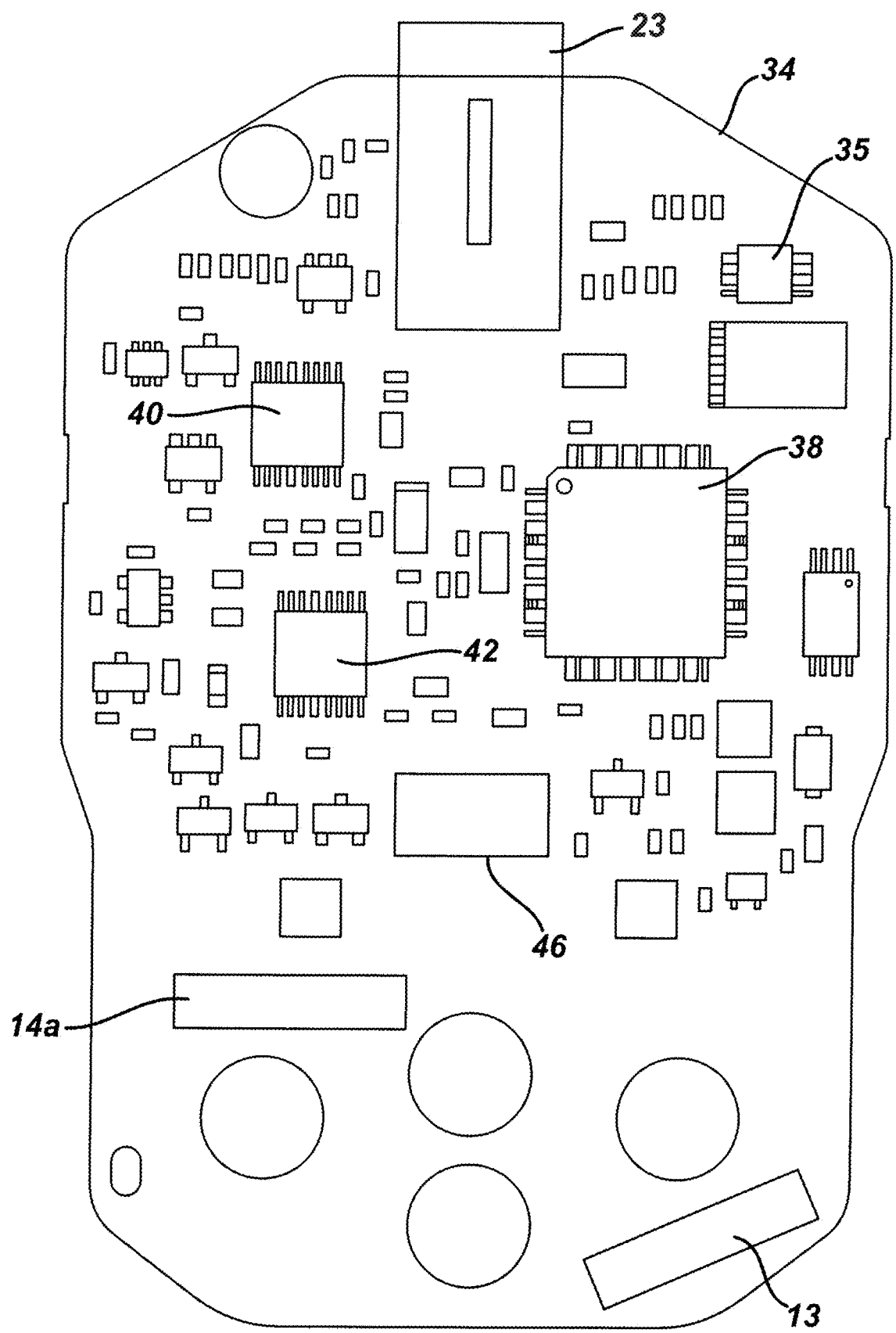
FIG. 2 is a top facing view of a circuit board disposed in the test meter of FIG. 1, depicting various components in accordance with aspects set forth herein.

As represented in FIG. 2 and shown in simplified schematic form, the electronic components of the portable test meter 10 may be disposed on a circuit board 34 contained within the interior of the housing 11, FIG. 1. According to this embodiment, the electronic components include a strip port connector 23, an operational amplifier circuit 35, a microcontroller 38, a display connector 14a, a non-volatile memory 40, a clock 42, and a first wireless module 46. On an opposing bottom surface of the circuit board 34, the electronic components may include a battery connector (not shown) and a data port 13. It will be understood that the relative position of the various electronic components can be varied and the configuration herein described is exemplary.

The microcontroller 38 may be electrically connected to the strip port connector 23 aligned with the strip port opening 22 (FIG. 1), the operational amplifier circuit 35, the first wireless module 46, the display 14, the non-volatile memory 40, the clock 42, at least one battery (not shown), a data port 13, and the user interface buttons (16, 18, and 20).

The operational amplifier circuit 35 may include two or more operational amplifiers configured to provide a portion of the potentiostat function and the current measurement function. The potentiostat function may refer to the application of a test voltage between at least two electrodes of a test strip. The current function may refer to the measurement of a test current resulting from the applied test voltage. The current measurement may be performed with a current-to-voltage converter. The microcontroller 38 may be in the form of a mixed signal microprocessor (MSP) 430 such as, for example, the Texas Instruments (TI) MSP. The MSP 430 may be configured to also perform a portion of the potentiostat function and the current measurement function. In addition, the 430 may also include volatile and non-volatile memory. In another embodiment, many of the electronic components may be integrated with the microcontroller in the form of an application specific integrated circuit (ASIC).

The strip port connector 23 may be configured to form an electrical connection to the test strip 62. The display connector 14a may be configured to attach to the display 14. For purposes of this description, the display 14 may be in the form of a liquid crystal display for reporting measured glucose levels, and for facilitating entry of lifestyle related information. The display 14 may optionally include a backlight. The data port 13 may accept a suitable connector attached to a connecting lead, thereby allowing the test meter 10 to be linked to an external device, such as a personal computer (not shown). For purposes of this description, the data port 13 may be any port that allows for transmission of data such as, for example, a serial, USB, or a parallel port. The data port 13 can be accessed through the housing 11 of the portable test meter 10. The clock 42 may be configured to keep current time related to the geographic region in which the user is located and also for measuring time. The test meter 10 may be configured to be electrically connected to a power supply such as, for example, at least one contained battery (not shown).

Figures 3D, 3E, 3F:
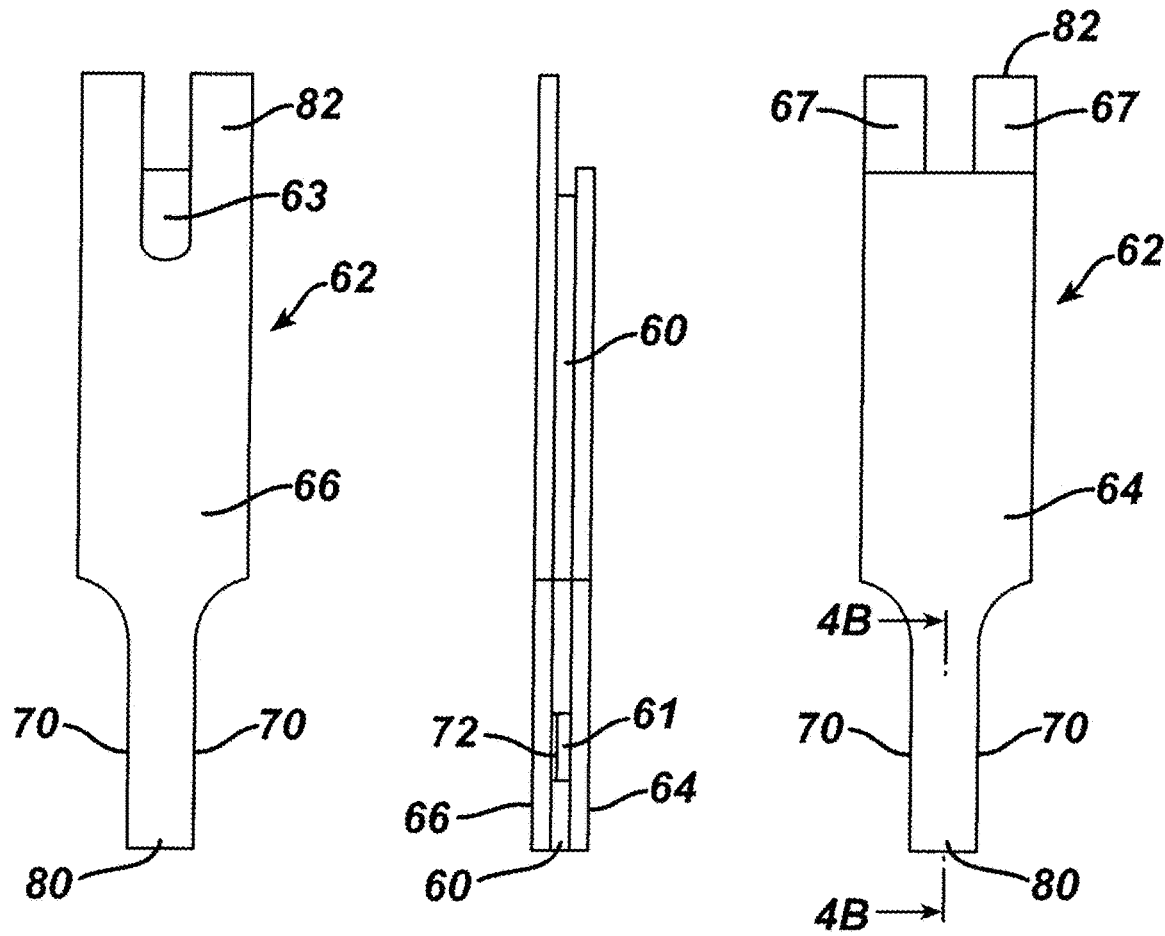
FIG. 3D is a bottom plan view of the test strip of FIGS. 3A-3C.
FIG. 3E is a side elevational view of the test strip of FIGS. 3A-3D.
FIG. 3F is a top plan view of the test strip of FIGS. 3A-3E.

FIGS. 3A-3G show various views of a test strip 62 suitable for use with the methods and systems described herein. In an exemplary embodiment, the test strip 62 is defined by an elongate body extending from a distal end 80 to an opposing proximal end 82, and having lateral edges 56, 58, as illustrated in FIG. 3A. As shown in FIG. 3B, the test strip 62 also includes a first electrode layer 66, a second electrode layer 64, and a spacer 60 sandwiched in between the two electrode layers 64 and 66 at the distal end 80 of the test strip 62. The first electrode layer 66 may include a first electrode 66, a first connection track 76, and a first contact pad 67, where the first connection track 76 electrically connects the first electrode 66 to the first contact pad 67, as shown in FIGS. 3B and 3C. Note that the first electrode 66 is a portion of the first electrode layer 66 that is immediately beneath the reagent layer 72, as indicated by FIGS. 3A and 3B. Similarly, the second electrode layer 64 may include a second electrode 64, a second connection track 78, and a second contact pad 63, where the second connection track 78 electrically connects the second electrode 64 with the second contact pad 63, as shown in FIGS. 3A-3C. Note that the second electrode 64 is a portion of the second electrode layer 64 that is disposed above the reagent layer 72, as best shown in FIGS. 3B and 3C.

Figure 3G:
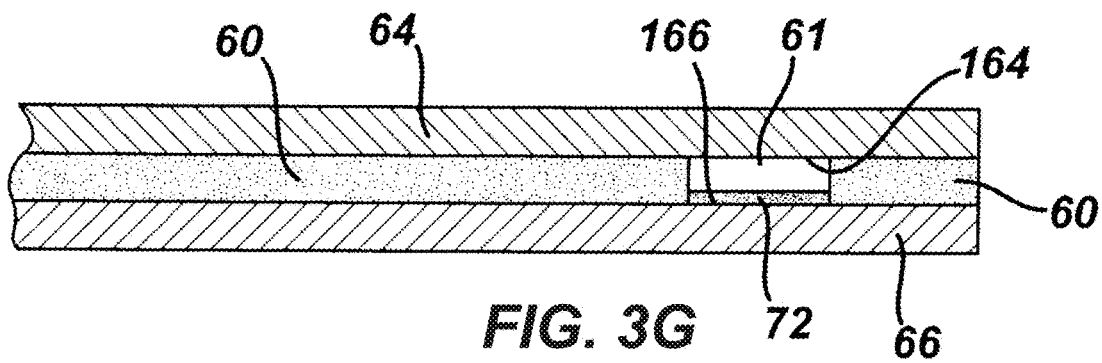
FIG. 3G is a partial side elevational view of a proximal portion of the test strip of FIGS. 3A-3F.

As shown, a sample-receiving chamber 61 (e.g., an electrochemical cell) is defined by the first electrode 66, the second electrode 64, and the spacer 60 proximate to the distal end 80 of the test strip 62, as shown in FIGS. 3B-3E. The first electrode 66 and the second electrode 64 may define the bottom and the top of sample-receiving chamber 61, respectively, as illustrated in FIG. 3G. A cutout area 68 of the spacer 60 may define the sidewalls of the sample-receiving chamber 61, as illustrated in FIG. 3G. In one aspect, the sample-receiving chamber 61 may include ports 70 that provide a sample inlet and/or a vent, as shown in FIGS. 3A-3C. For example, one of the ports 70 may allow a fluid sample to ingress and the other port 70 may allow air to egress.

In an exemplary embodiment, the sample-receiving chamber 61 may have a small volume. For example, the chamber 61 may have a volume in the range of from about 0.1 microliters to about 5 microliters, about 0.2 microliters to about 3 microliters, or, preferably, about 0.3 microliters to about 1 microliter. To provide the small sample volume, the cutout 68 may have an area ranging from about 0.01 $cm^2$ to about 0.2 $cm^2$, about 0.02 $cm^2$ to about 0.15 $cm^2$, or, preferably, about 0.03 $cm^2$ to about 0.08 $cm^2$. In addition, first electrode 66 and second electrode 64 may be spaced apart in the range of about 1 micron to about 500 microns, preferably between about 10 microns and about 400 microns, and more preferably between about 40 microns and about 200 microns. The relatively close spacing of the electrodes may also allow redox cycling to occur, where oxidized mediator generated at the first electrode 66, may diffuse to the second electrode 64 to become reduced, and subsequently diffuse back to the first electrode 66 to become oxidized again. Those skilled in the art will appreciate that various such volumes, areas, and/or spacing of electrodes is within the spirit and scope of the present disclosure.

In one embodiment, the first electrode 66 and the second electrode 64 may each include an electrode layer. The electrode layer may include a conductive material formed from materials such as gold, palladium, carbon, silver, platinum, tin oxide, iridium, indium, or combinations thereof (e.g., indium doped tin oxide). In addition, the electrode layers may be formed by disposing a conductive material onto an insulating sheet (not shown) by a sputtering, electroless plating, or a screen-printing process. In one exemplary embodiment, the first electrode 66 and the second electrode 64 may each include electrode layers made from sputtered palladium and sputtered gold, respectively. Suitable materials that may be employed as spacer 60 include a variety of insulating materials, such as, for example, plastics (e.g., PET, PETG, polyimide, polycarbonate, polystyrene), silicon, ceramic, glass, adhesives, and combinations thereof.

In one embodiment, the spacer 60 may be in the form of a double sided adhesive coated on opposing sides of a polyester sheet where the adhesive may be pressure sensitive or heat activated. Applicants note that various other materials for the first electrode layer 66, the second electrode layer 64, and/or the spacer 60 are within the spirit and scope of the present disclosure.

Either the first electrode 66 or the second electrode 64 may perform the function of a working electrode depending on the magnitude and/or polarity of at least one applied test voltage. The working electrode may measure a limiting test current that is proportional to the reduced mediator concentration. For example, if the current limiting species is a reduced mediator (e.g., potassium ferrocyanide), then it may be oxidized at the first electrode 66 as long as the test voltage is sufficiently greater than the redox mediator potential with respect to the second electrode 64. In this situation, the first electrode 66 performs the function of the working electrode and the second electrode 64 performs the function of a counter/reference electrode. Applicants note that one may refer to a counter/reference electrode simply as a reference electrode or a counter electrode. A limiting oxidation occurs when all of the reduced mediator has been depleted at the working electrode surface such that the measured oxidation current is proportional to the flux of reduced mediator diffusing from the bulk solution towards the working electrode surface. The term "bulk solution" as used herein refers to a portion of the solution sufficiently far away from the working electrode where the reduced mediator is not located within a depletion zone. It should be noted that unless otherwise stated for the test strip 62, all potentials applied by the test meter 10 will hereinafter be stated with respect to the second electrode 64.

Similarly, if the test voltage is sufficiently less than the redox mediator potential, then the reduced mediator may be oxidized at the second electrode 64 as a limiting current. In such a situation, the second electrode 64 performs the function of the working electrode and the first electrode 66 performs the function of the counter/reference electrode.

Initially, an analysis may include introducing a quantity of a fluid sample into the sample-receiving chamber 61 via one of the ports 70. In one aspect, the port 70 and/or the sample-receiving chamber 61 may be configured such that capillary action causes the fluid sample to fill the sample-receiving chamber 61. The first electrode 66 and/or second electrode 64 may be coated with a hydrophilic reagent to promote the capillarity of the sample-receiving chamber 61. For example, thiol derivatized reagents having a hydrophilic moiety, such as 2-mercaptoethane sulfonic acid, may be coated onto the first electrode and/or the second electrode.

In the analysis of the test strip 62 above, the reagent layer 72 can include glucose dehydrogenase (GDH) based on the PQQ co-factor and ferricyanide. In another embodiment, the enzyme GDH based on the PQQ co-factor may be replaced with the enzyme GDH based on the FAD co-factor. When blood or control solution is dosed into a sample reaction chamber 61, glucose is oxidized by $GDH_{(ox)}$ and in the process, converts $GDH_{(ox)}$ to $GDH_{(red)}$, as shown in the chemical transformation T.1 below. Note that $GDH_{(ox)}$ refers to the oxidized state of GDH, and $GDH_{(red)}$ refers to the reduced state of GDH.

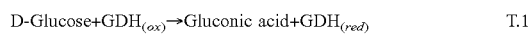

D-Glucose+$GDH_{(ox)}$→Gluconic acid+$GDH_{(red)}$  T.1

Next, $GDH_{(red)}$ is regenerated back to its active oxidized state by ferricyanide (i.e. oxidized mediator or $Fe(CN)_6^{3-}$, such as potassium ferricyanide) as shown in chemical transformation T.2 below. In the process of regenerating $GDH_{(ox)}$, ferrocyanide (i.e. reduced mediator or $Fe(CN)_6^{4-}$, such as potassium ferrocyanide) is generated from the reaction as shown in T.2:

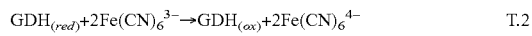

$GDH_{(red)}$+2$Fe(CN)_6^{3-}$→$GDH_{(ox)}$+2$Fe(CN)_6^{4-}$  T.2

Figure 4:
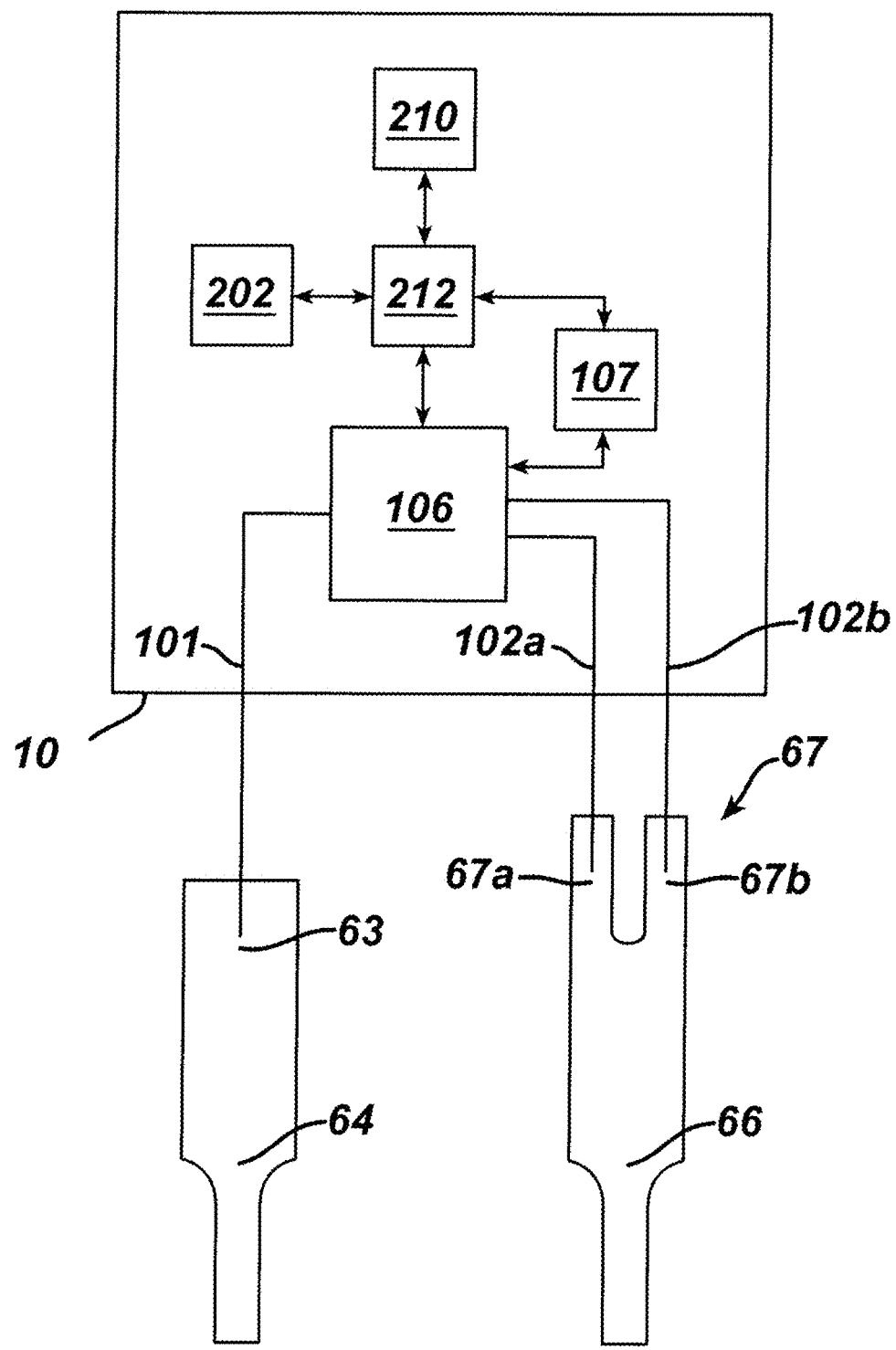
FIG. 4 is a simplified schematic diagram showing a test meter electrically interfacing with portions of a test strip, such as the test strip depicted in FIGS. 3A-3F.

FIG. 4 provides a simplified schematic showing a test meter 10 interfacing with a first contact pad 67a, 67b and a second contact pad 63 of the test strip 62. The second contact pad 63 may be used to establish an electrical connection to the test meter 10 through a U-shaped notch 65, as illustrated in FIG. 3B. In one embodiment, the test meter 10 may include a second electrode connector 101, first electrode connectors (102a, 102b), a test voltage unit 106, a current measurement unit 107, a processor 212, a memory unit 210, and a visual display 202, as schematically shown in FIG. 4. The first contact pad 67 may include two prongs denoted as 67a and 67b. In one exemplary embodiment, the first electrode connectors 102a and 102b separately connect to prongs 67a and 67b, respectively. The second electrode connector 101 may connect to the second contact pad 63. The test meter 10 may measure the resistance or electrical continuity between the prongs 67a and 67b to determine whether the test strip 62 is electrically connected to the test meter 10.

In one embodiment, the test meter 10 may apply a test voltage and/or a current between the first contact pad 67 and the second contact pad 63. Once the test meter 10 recognizes that the strip 62 has been inserted, the test meter 10 is powered on and initiates a fluid detection mode. In one embodiment, the fluid detection mode causes the test meter 10 to apply a constant current of about 1 microampere between the first electrode 66 and the second electrode 64. Because the test strip 62 is initially dry, the test meter 10 measures a relatively large voltage. When the fluid sample bridges the gap between the first electrode 66 and the second electrode 64 during the dosing process, the test meter 10 will measure a decrease in measured voltage that is below a predetermined threshold causing the test meter 10 to automatically initiate a glucose test.

Referring to FIGS. 5A-5D, a method for determining an analyte concentration, using a test strip 62 and the test meter 10, will now be described. By way of overview, first, application of the test voltages and measurement of current values will be discussed, followed by an explanation of analyte concentration measurement.

First, with respect to the application of voltages to the test strip, example test meter 10 and example test strip 62 are references. The test meter 10 may include electronic circuitry that can be used to apply a plurality of voltages to the test strip 62 and to measure a current transient output resulting from an electrochemical reaction in a test chamber of the test strip 62. The test meter 10 also may include a signal processor with a set of instructions for the method of determining an analyte concentration in a fluid sample as disclosed herein. In one embodiment, the analyte is blood glucose.

Continuing with the discussion of application of test voltages, FIG. 5A sets forth an exemplary waveform consisting of a plurality of test voltages applied to the test strip 62 for prescribed time intervals. The plurality of test voltages according to this waveform include a first test voltage E1 that is applied for a first time interval $t_1$, a second test voltage E2 that is applied for a second time interval $t_2$, and a third test voltage E3 applied for a third time interval $t_3$. The third voltage E3 may be different in the magnitude of the electromotive force, in polarity, or combinations of both with respect to the second test voltage E2. In the preferred embodiments and as shown, E3 may be of the same magnitude as E2 but opposite in polarity. A glucose test time interval $t_G$ represents an amount of time to perform the glucose test (but not necessarily all the calculations associated with the glucose test). Glucose test time interval $t_G$ may range from about 1.1 seconds to about 5 seconds. Further, as illustrated in FIG. 5A, the second test voltage E2 may include a constant (DC) test voltage component and a superimposed alternating (AC), or alternatively oscillating, test voltage component applied for a short time interval. More specifically, the superimposed alternating or oscillating test voltage component may be applied for a time interval indicated by $t_{cap}$ at the initiation of the second time interval.

The plurality of test current values measured during any of the time intervals may be performed at a frequency ranging from about 1 measurement per microsecond to about one measurement per 100 milliseconds and preferably at about 10 milliseconds. While an embodiment using three test voltages in a serial manner is described, the glucose test may include different numbers of open-circuit and test voltages.

Figure 5C:
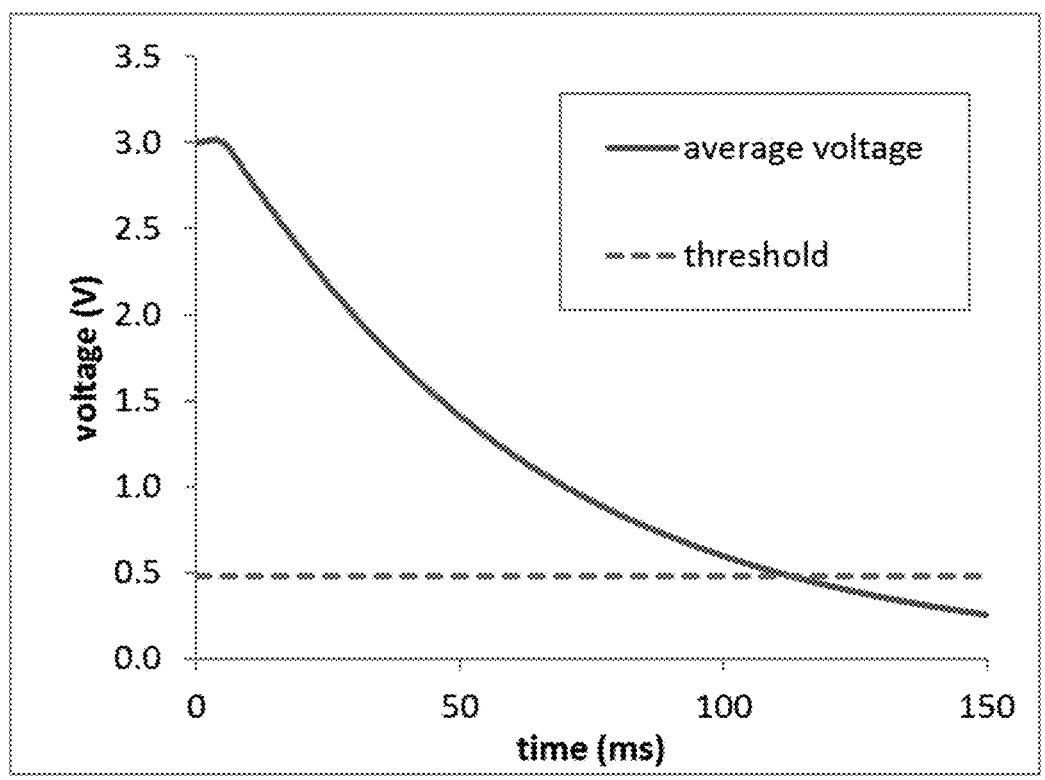
FIG. 5C depicts triggering of the test waveform of FIG. 5A based upon determining that the sample has filled the test strip depicted in FIGS. 3A-3F.

FIG. 5C depicts triggering of the test waveform of FIG. 5A based upon determining that the sample has filled the test strip 62 depicted in FIGS. 3A-3F. For instance, during a test cycle, a user may apply a blood sample to the test strip, and during the early stages of application, the test strip 62 will begin to fill with the sample. At this time, the signal can be quite noisy as the sample physically enters the electrochemical cell. In order to best determine when to begin testing the sample, a triggering current of 500-700 nA may be applied between the electrodes, and average voltage values may be measured as depicted in FIG. 5C. When the voltage value drops from approximately 3.0 V to a predetermined value, for example, 0.5 V, the test waveform of FIG. 5A may be triggered, and the test cycle started. Advantageously, waiting for the average voltage to fall below the predetermined threshold value will allow time for the noisy signal to dissipate before testing.

Figure 5D:
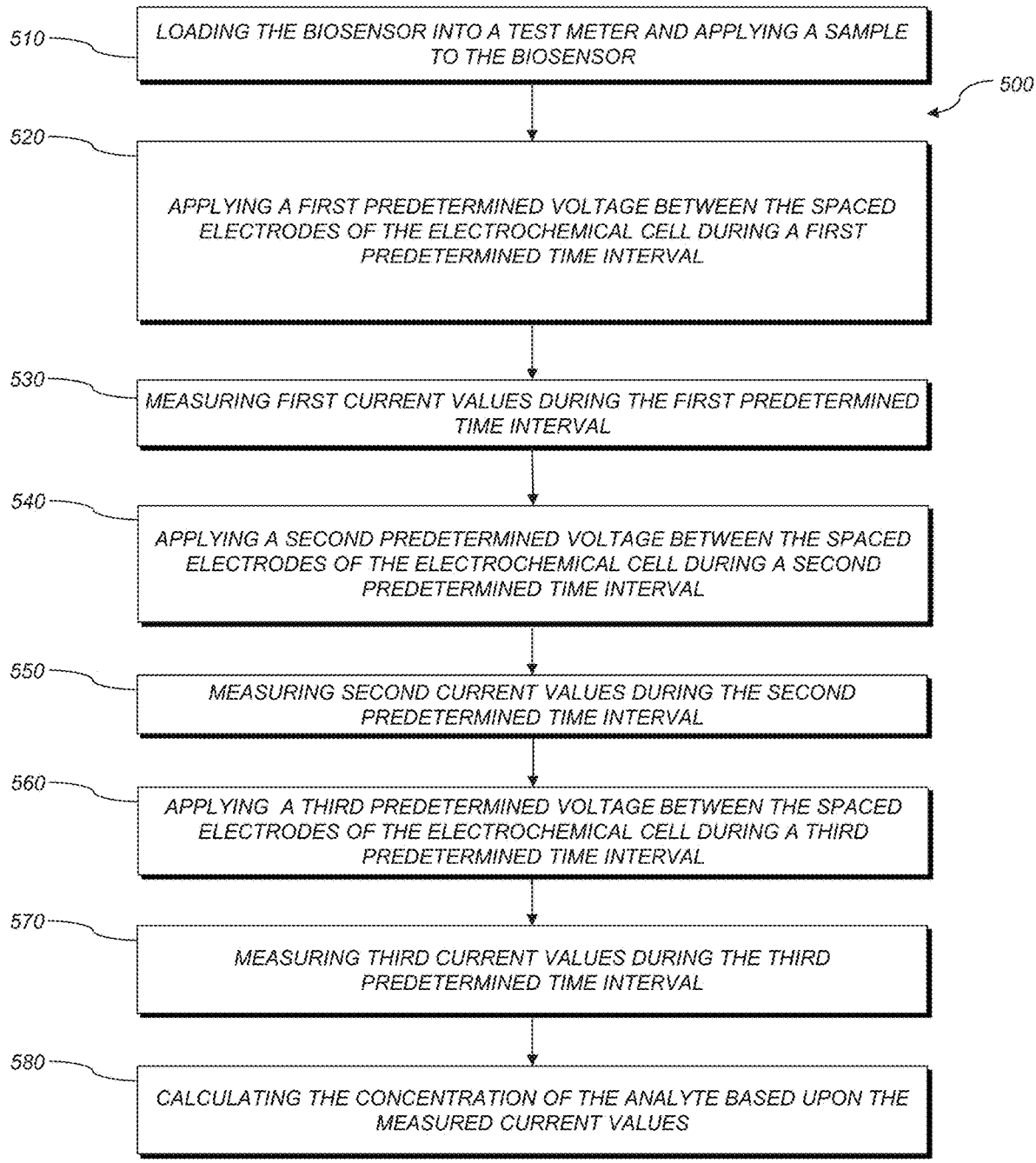
FIG. 5D is a flowchart representing a method for determining analyte concentration in a test strip.

FIG. 5D is a flowchart representing a method 500 for determining analyte concentration in a test strip, based on the waveform of FIG. 5A and measured currents as shown in FIG. 5B. In exemplary step 510, the glucose assay is initiated by inserting a test strip 62 into the test meter 10 and by depositing a sample on the test strip 62. In exemplary step 520, the test meter 10 may apply a first test voltage E1 (e.g., approximately 20 mV in FIG. 5A) between the first electrode 66 and the second electrode 64 for a first time interval $t_1$ (e.g., 1 second in FIG. 5A). The first time interval $t_1$ may range from about 0.1 seconds to about 3 seconds and preferably range from about 0.2 seconds to about 2 seconds, and most preferably range from about 0.3 seconds to about 1.1 seconds.

The first time interval $t_1$ may be sufficiently long so that the sample-receiving chamber 61 may fully fill with sample and also so that the reagent layer 72 may at least partially dissolve or solvate. In one aspect, the first test voltage E1 may be a value relatively close to the redox potential of the mediator so that a relatively small amount of a reduction or oxidation current is measured. FIG. 5B shows that a relatively small amount of current is observed during the first time interval $t_1$ compared to the second and third time intervals $t_2$ and $t_3$. For example, when using potassium ferricyanide and/or potassium ferrocyanide as the mediator, the first test voltage E1 in FIG. 5A may range from about 1 mV to about 100 mV, preferably range from about 5 mV to about 50 mV, and most preferably range from about 10 mV to about 30 mV. Although the applied voltages are given as positive values in the preferred embodiments, the same voltages in the negative domain could also be utilized to accomplish the intended purpose of the claimed invention. During this interval, the first current output may be sampled by the processor to collect current values over this interval in step 530.

In exemplary step 540, after applying the first test voltage E1 (step 520) and sampling the output (step 530), the test meter 10 applies a second test voltage E2 between first electrode 66 and second electrode 64 (e.g., approximately 300 millivolts in FIG. 5A), for a second time interval $t_2$ (e.g., about 3 seconds in FIG. 5A). The second test voltage E2 may be a value different than the first test voltage E1 and may be sufficiently negative of the mediator redox potential so that a limiting oxidation current is measured at the second electrode 64. For example, when using potassium ferricyanide and/or potassium ferrocyanide as the mediator, the second test voltage E2 may range from about zero mV to about 600 mV, preferably range from about 100 mV to about 600 mV, and more preferably is about 300 mV.

The second time interval $t_2$ should be sufficiently long so that the rate of generation of reduced mediator (e.g., potassium ferrocyanide) may be monitored based on the magnitude of a limiting oxidation current. Reduced mediator is generated by enzymatic reactions with the reagent layer 72. During the second time interval $t_2$, a limiting amount of reduced mediator is oxidized at second electrode 64 and a non-limiting amount of oxidized mediator is reduced at first electrode 66 to form a concentration gradient between the first electrode 66 and the second electrode 64.

In an exemplary embodiment, the second time interval $t_2$ should also be sufficiently long so that a sufficient amount of potassium ferricyanide may be diffused to the second electrode 64 or diffused from the reagent on the first electrode. A sufficient amount of potassium ferricyanide is required at the second electrode 64 so that a limiting current may be measured for oxidizing potassium ferrocyanide at the first electrode 66 during the third test voltage E3. The second time interval $t_2$ may be less than about 60 seconds, and preferably may range from about 1.1 seconds to about 10 seconds, and more preferably range from about 2 seconds to about 5 seconds. Likewise, the time interval indicated as $t_{cap}$ in FIG. 5A may also last over a range of times, but in one exemplary embodiment it has a duration of about 20 milliseconds. In one exemplary embodiment, the superimposed alternating test voltage component is applied after about 0.3 seconds to about 0.4 seconds after the application of the second test voltage E2, and induces a sine wave having a frequency of about 109 Hz with an amplitude of about +/−50 mV. During this interval, a second current output may be sampled by the processor to collect current values over this interval in step 550.

FIG. 5B shows a relatively small current $i_{pb}$ after the beginning of the second time interval $t_2$ followed by a gradual increase of an absolute value of an oxidation current during the second time interval $t_2$. The small current $i_{pb}$ occurs due to oxidation of endogenous or exogenous reducing agents after a transition from first voltage E1 to second voltage E2 leading to a gradual increase of an absolute value of an oxidation current during the second time interval $t_2$.

In exemplary step 560, after applying the second test voltage E2 (step 540) and sampling the output (step 550), the test meter 10 applies a third test voltage E3 between the first electrode 66 and the second electrode 64 (e.g., about −300 millivolts in FIG. 5A) for a third time interval $t_3$ (e.g., 1 second in FIG. 5A). The third test voltage E3 may be a value sufficiently positive of the mediator redox potential so that a limiting oxidation current is measured at the first electrode 66. For example, when using potassium ferricyanide and/or potassium ferrocyanide as the mediator, the third test voltage E3 may range from about zero mV to about −600 mV, preferably range from about −100 mV to about −600 mV, and more preferably is about −300 mV.

After applying the third test voltage E3, in step 570 current values are measured in the third time interval $t_3$. The third time interval $t_3$ may be sufficiently long to monitor the diffusion of reduced mediator (e.g., potassium ferrocyanide) near the first electrode 66 based on the magnitude of the oxidation current. During the third time interval $t_3$, a limiting amount of reduced mediator is oxidized at the first electrode 66 and a non-limiting amount of oxidized mediator is reduced at the second electrode 64. The third time interval $t_3$ may range from about 0.1 seconds to about 5 seconds and preferably range from about 0.3 seconds to about 3 seconds, and more preferably range from about 0.5 seconds to about 2 seconds.

FIG. 5B shows a relatively large current $i_{pc}$ at the beginning of the third time interval $t_3$ followed by a decrease to a nearly steady-state current $i_{ss}$ value, for a nominal test strip. In one embodiment, the second test voltage E2 may have a first polarity and the third test voltage E3 may have a second polarity that is opposite to the first polarity. In another embodiment, the second test voltage E2 may be sufficiently negative of the mediator redox potential and the third test voltage E3 may be sufficiently positive of the mediator redox potential. The third test voltage E3 may be applied immediately after the second test voltage E2. However, one skilled in the art will appreciate that the magnitude and polarity of the second and third test voltages may be chosen depending on the manner in which analyte concentration is determined.

Next, glucose concentration determination is described for the embodiments described herein, and as set forth in step 580 of FIG. 5D. FIGS. 5A and 5B show the sequence of events in the test strip transient. At approximately 1.1 seconds after initiation of the test sequence (and shortly after making the second electrode the working electrode due to application of the second voltage E2), when no reagent has yet reached the first electrode, and current is due predominantly to interfering reducing agents in plasma (in the absence of mediator at the second electrode 64), a current measurement is taken. Between about 1.4 seconds and about 4 seconds, when (at least in the latter part of this interval when a second voltage E2 is applied) the reduced mediator has diffused to the second electrode, a first glucose-proportional current, $i_1$, is measured. Shortly after making the first electrode the working electrode via application of the third voltage E3, 2 single-point measurements (at approximately 4.1 and 5 seconds according to this embodiment) and one integrated measurement $i_r$ are taken. The measurements sampled respectively at 1.1, 4.1 and 5 seconds according to this specific embodiment are used to correct $i_r$ for additive current from interfering reducing agents (i2corr). The ratio of $i_1$ to $i_r$ is used to correct i2corr for the interfering effects of hematocrit.

In one embodiment, the following equation is then used to determine the glucose concentration:

$$G_{basic} = \left(\left|\frac{i_r}{i_l}\right|\right)^p \cdot (a \cdot |i_{2corr}| - z_{gr}),$$

$G_{basic}$ is the analyte concentration;
$i_r$ is the sum of the third current values during the third time interval;
$i_l$ is the sum of the second current values during the second time interval;

$$i_{2corr} = \frac{|i_{pc}| + b|i_{ss}| - 2|i_{pb}|}{|i_{pc}| + b|i_{ss}|} \cdot i_r;$$

and
a, b, p are $z_{gr}$, predetermined coefficients.
In one specific example, $$i_{2corr} = \frac{|i(4.1\,s)| + b|i(5\,s)| - 2|i(1.1\,s)|}{|i(4.1\,s)| + b|i(5\,s)|} \cdot i_r$$

In another example, different test strip chemistries may be used, in which the times that appear in the current evaluation are changed in accordance with the above generic relation. Additional details relating to the applied waveform and the determination of analyte concentration of a test strip are provided in U.S. Pat. No. 8,709,232 B2 and International Patent Publication No. WO 2012/012341 A1, previously incorporated by reference herein.

FIGS. 6A-6H provide a working example of the technique set forth herein

Figure 6A:
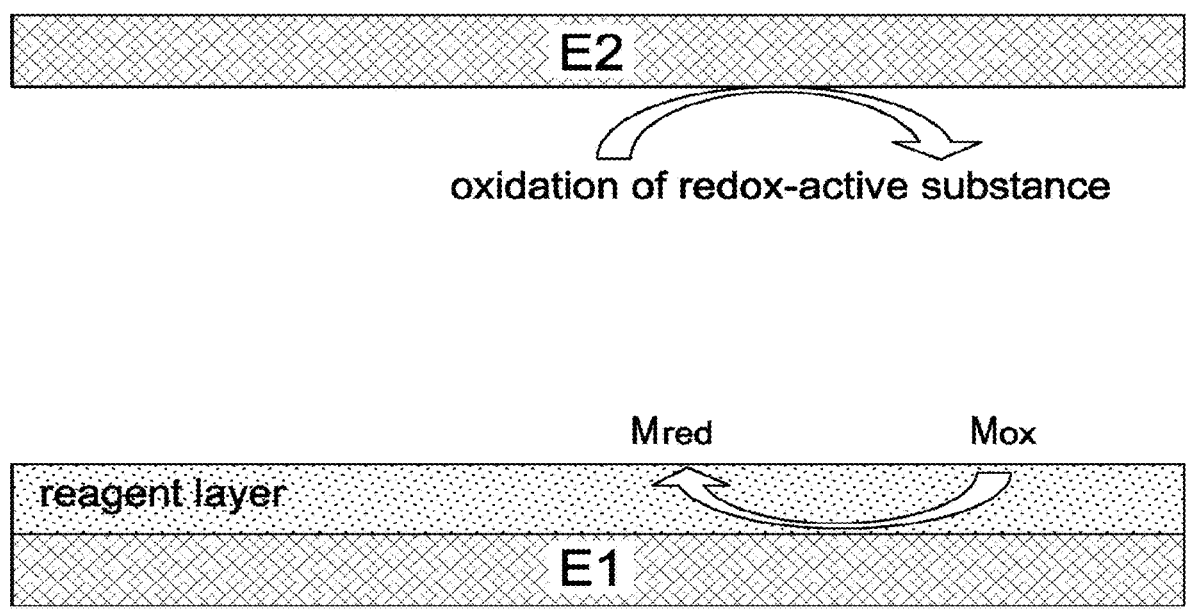
FIG. 6A depicts a redox reaction at two electrodes stimulated by applying an electrical potential between the electrodes.

Beginning first with FIG. 6A, the underlying mechanism for the measurement issues are identified. In FIG. 6A, redox reactions are depicted for an electrochemical test strip, for example a self-monitoring blood glucose test strip 62 of FIG. 1. The example strip has two electrodes, a first electrode E1 and second electrode E2. However, similar results are obtained with three or more electrodes, and the electrodes may be co-facial, co-planar, or have other spaced apart configurations. The first electrode E1 is covered with a reagent layer which contains redox mediator (M) and other materials (e.g. enzyme) while the second electrode E2 has a surface without the covering reagent layer. The first and second electrodes E1 and E2, respectively, are electrically connected to a potentiostat (not shown). In use, the first and second electrodes E1 and E2, respectively, are in contact with a whole blood sample and an electric potential (voltage) is applied between the two electrodes. This results in redox reactions at the both electrodes. The resulting current between the first and second electrodes E1 and E2 is measured as a function of time.

To conduct a test using the test strip, an electric potential is applied between the first and second electrodes E1 and E2, and the resulting current is measured. The magnitude and polarity of the electric potential are chosen to initiate a reduction(s) of the mediator(s) at the first electrode E1 and an oxidation(s) of redox-active substance(s) at the second electrode E2.

Applying a blood sample to the strip sample chamber triggers physical and chemical processes/changes which depend on physical characteristic(s) (e.g., haematocrit) and redox-active substance(s) of the blood sample. The physical processes include hydration of the reagent layer, dissolution of the mediator, and double-layer charging (a process to neutralize the charge imbalance near the electrode surfaces by rearrangement of charged species in the blood). The chemical processes include oxidation(s) of the redox-active substance(s) at the second electrode E2 and reduction of the oxidized mediator $M_{ox}$ at the first electrode E1, as shown in FIG. 1.

Figure 6B:
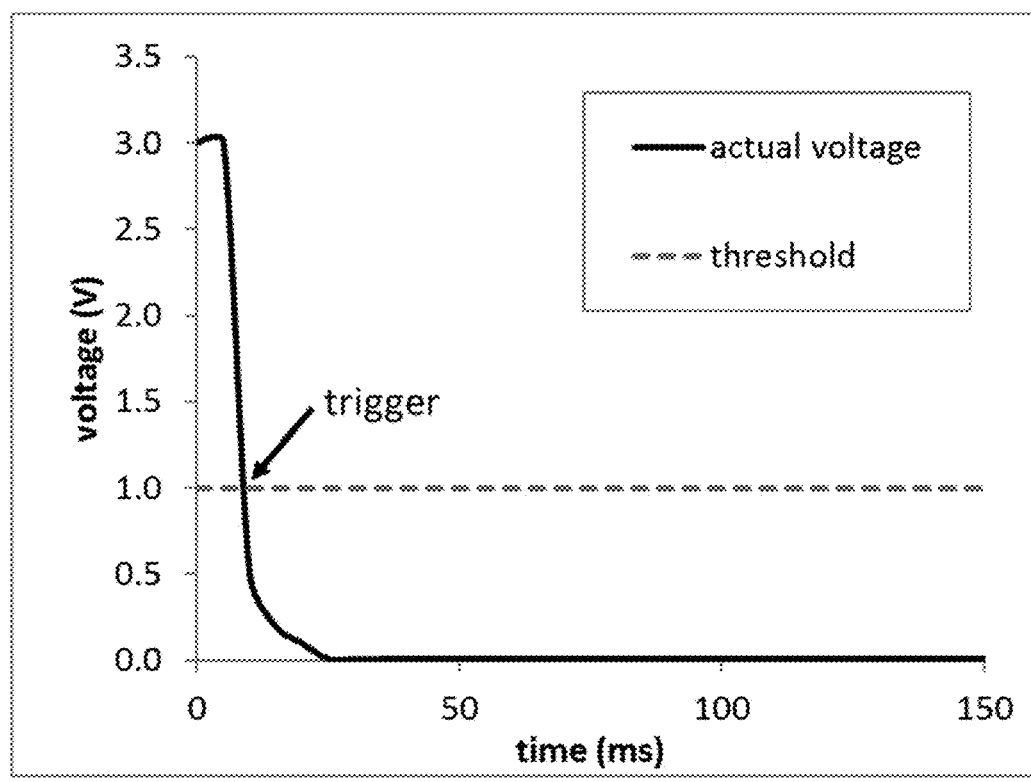
FIG. 6B depicts triggering based upon determining that the sample has been applied to the test strip depicted in FIGS. 3A-3F.
Figure 6C:
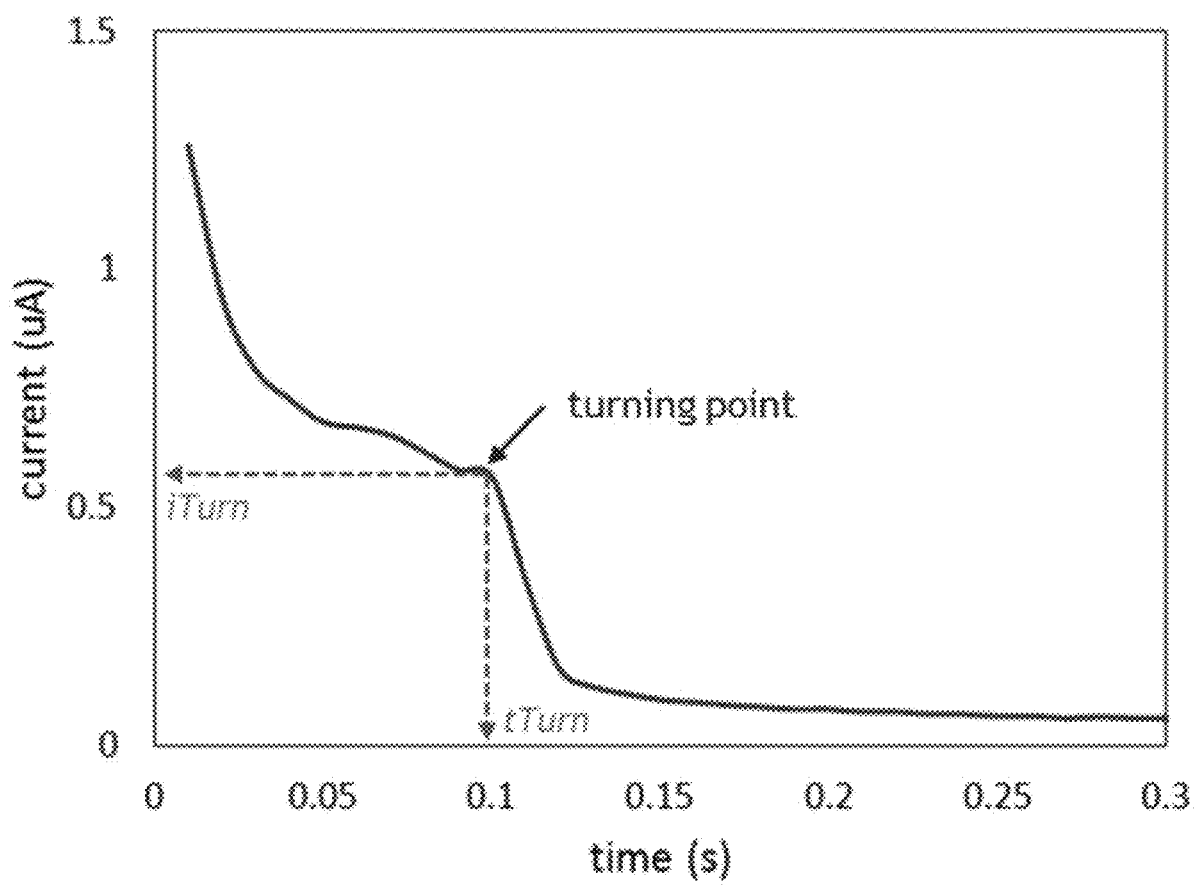
FIG. 6C depicts a plot of current versus time measured after application of the electrical potential, including a turning point at which the current profile transitions from, e.g., a non-Cottrell profile to, e.g., a Cottrell profile.

As a result of the physical and chemical processes noted above, the recorded current has a transient that has a unique pattern which deviates from a known Cottrell current decay profile, as depicted in FIG. 6C. However, the triggering for sample fill described with respect to FIG. 5C would occur too late to see this unique pattern.

Thus, FIG. 6B depicts earlier triggering based upon determining that the sample has been applied to the test strip depicted in FIGS. 3A-3F. In this example, a user may apply a blood sample to the test strip, and during the early stages of application, the test strip will begin to fill with the sample as noted above with respect to FIG. 5C, and a triggering current of 500-700 nA may be applied between the electrodes, and voltage values may be measured. By contrast with FIG. 5C, when the voltage value drops from approximately 3.0 V to a higher predetermined value, for example, 1.0 V, the test waveform of FIG. 5A may be triggered, and the test cycle started. Advantageously, this earlier triggering allows monitoring of some of the earlier electrochemical behavior, including observing the turning point depicted in FIG. 6C.

Figure 6D:
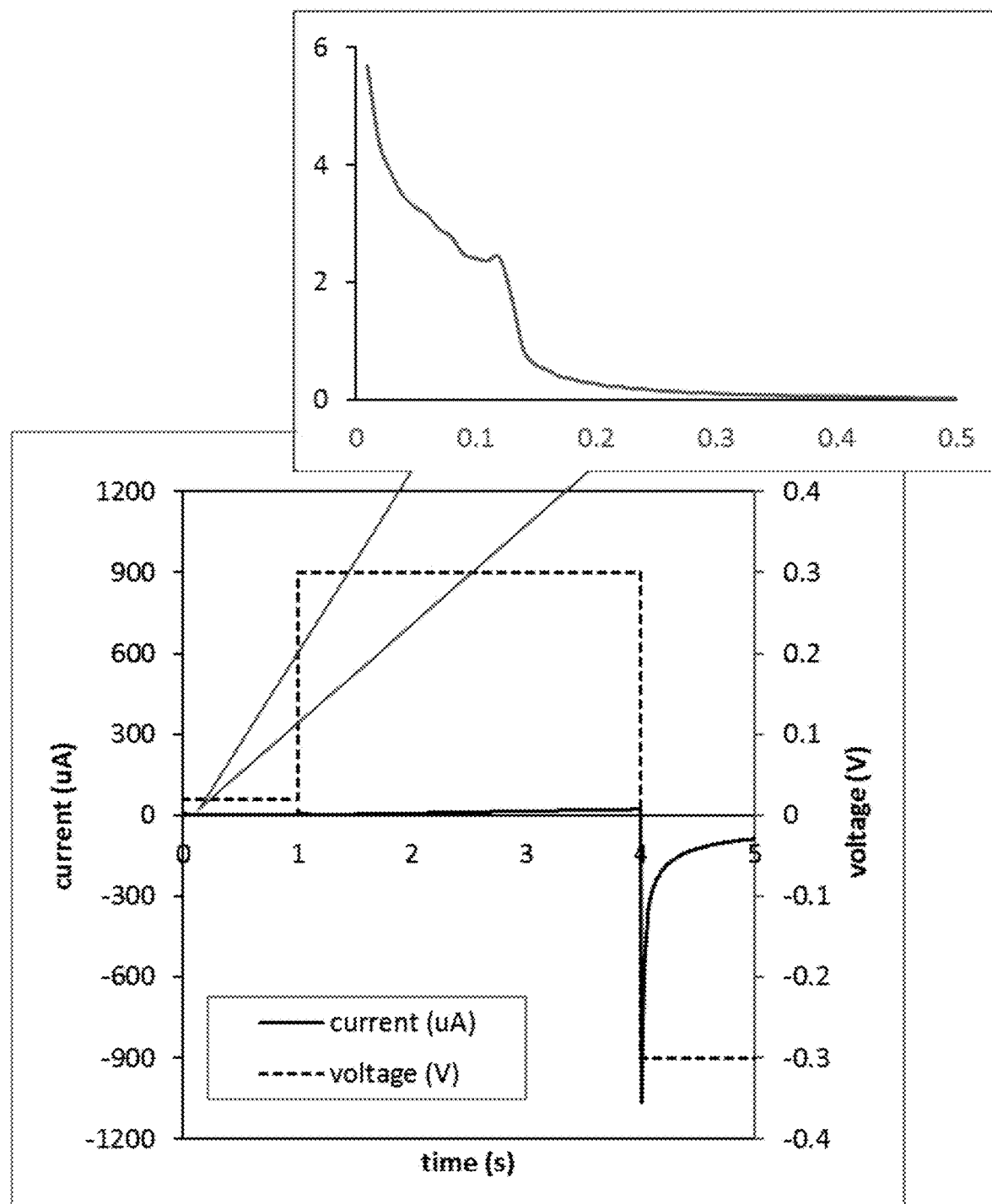
FIG. 6D depicts measured current values of the test strip depicted in FIGS. 3A-3F based upon the test waveform of FIG. 5A triggered as depicted in FIG. 6B.
Figure 6E:
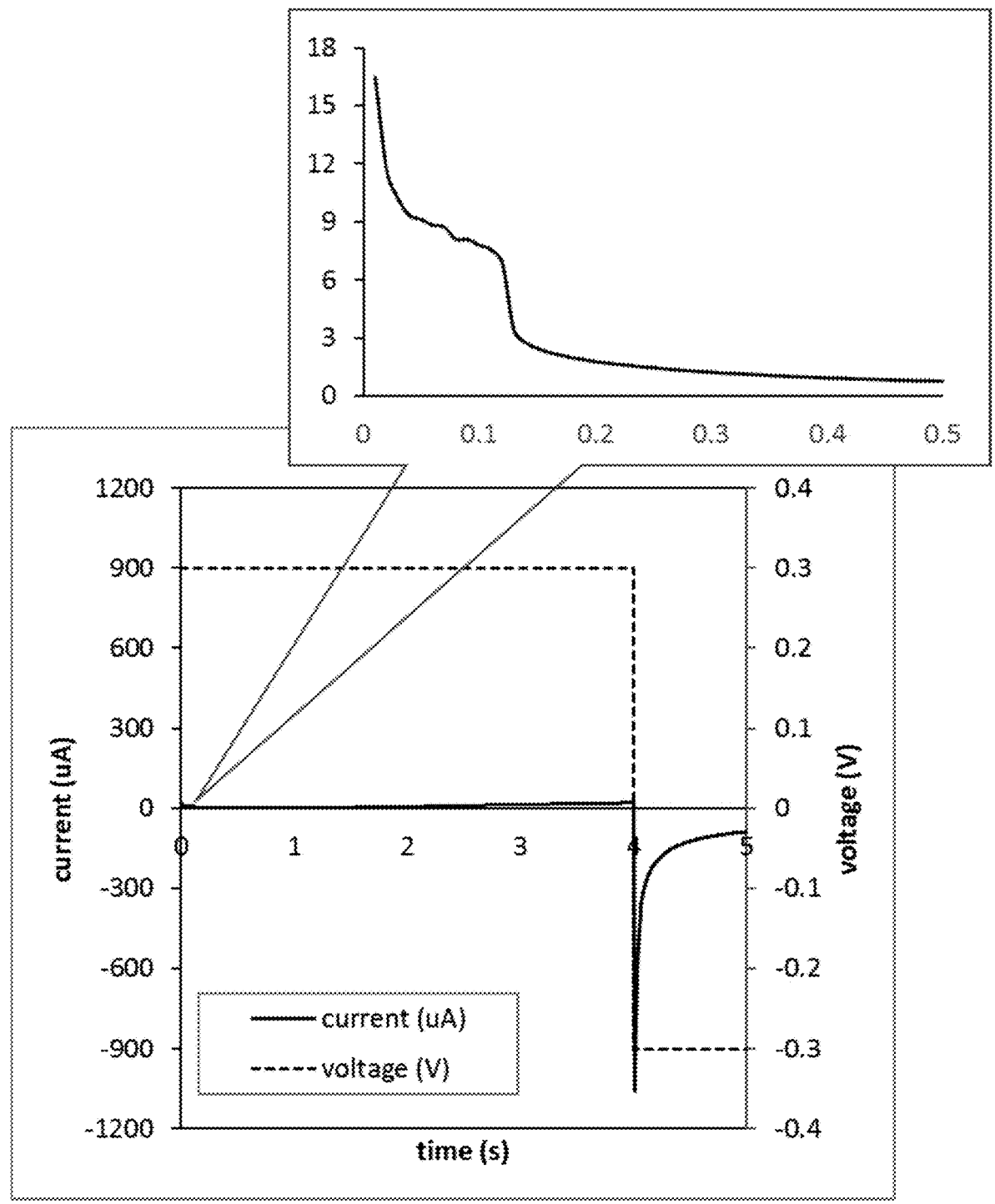
FIG. 6E depicts measured current values of the test strip depicted in FIGS. 3A-3F based on another waveform triggered as depicted in FIG. 6B.

FIG. 6C, depicts a plot of current versus time measured after application of the electrical potential, including the turning point at which the current profile transitions from, e.g., a non-Cottrell profile to, e.g., a Cottrell profile. FIG. 6D depicts measured current values of the test strip depicted in FIGS. 3A-3F based upon test waveform of FIG. 5A. FIG. 6E depicts measured current values of the test strip depicted in FIGS. 3A-3F based another waveform. In this example, the different waveform also exhibits a turning point as described above.

In each of the current plots of FIG. 6C-6E, a turning-point is noted, and has a current parameter $i_{Turn}$ and a time parameter $i_{Turn}$. The turning point is the point at which a first transient part with low level oscillations ends, and a second transient part with a smooth current decay begins. The first transient part deviates from Cottrell current decay profile while the second transient part substantially follows Cottrell current decay profile. The second transient part ends as soon as the current reaches a steady state or the redox mediator arrives at the second electrode E2 by diffusion from the reagent layer. The turning point may be identified by a process(es)/algorithm(s) which may be developed using various mathematical approaches/techniques.

Without wishing to be limited by theory, the deviation of the current transient from Cottrell current decay, in particular the first transient part, appears to result from the physical processes that play a predominant role at this stage in changing the active surface area of the first electrode E1 and/or availability of the mediator for the reduction at the first electrode E1. These physical processes appear to be dependent on diffusion of the blood sample. Regardless of the underlying physical mechanism, the time at which the transient current transitions from the first transient part to the second transient part, $t_{Turn}$, is a function of diffusion.

Again, without wishing to be limited by theory, at an early stage of a test using a test strip, the reduced mediator appears to not diffuse across the sample chamber to reach the surface of the second electrode E2. Hence, the oxidation current appears to be predominantly generated by the oxidation of redox-active substance(s). At the same time, the oxidation of redox-active substance(s) is dependent on mass transfer of the redox-active substance(s) in the fluidic sample. Regardless of the underlying physical mechanism, $i_{Turn}$ is a function of both the redox-active substance(s) and its diffusion.

The function for $t_{Turn}$ and the function for $i_{Turn}$ may be derived from laboratory data obtained by testing fluidic samples with designated diffusion property and redox-active substance(s). This allows determination of diffusion related features, such as for example, diffusion coefficient, hematocrit (which impacts diffusion), coagulation or viscosity. To allow the contribution of any redox-active substance(s) to be measured, the redox-active substance(s) of interest has to be calibrated as a function of the turning time $t_{Turn}$ and additionally as a function of turning current $i_{Turn}$. Alternatively, the redox-active substance(s) of interest could be represented by a mathematical function that is dependent on the turning time $i_{Turn}$ and the turning current $i_{Turn}$. In either case, once the relationship between the redox-active substance(s), the turning time $i_{Turn}$ and the turning current $i_{Turn}$ is known, it can be used in later measurements to provide a measure or estimate of the redox-active substance(s) or of the contribution to the measured current made by the redox-active substance(s).

The measure of the redox-active substance(s) may be a measure of the substance concentration in the sample. The measure of the contribution made by the redox-active substance(s) may be a measure of the contribution to the current. This can be used in subsequent steps or processes to correct any calculations based on the current measurements, when such calculations require the effects of the redox-active substance(s) to be excluded. For example, uric acid interferes with electrochemical glucose measurements, and the invention would allow the effects of the uric acid to be identified and excluded from any calculation of glucose levels.

Figure 6F:
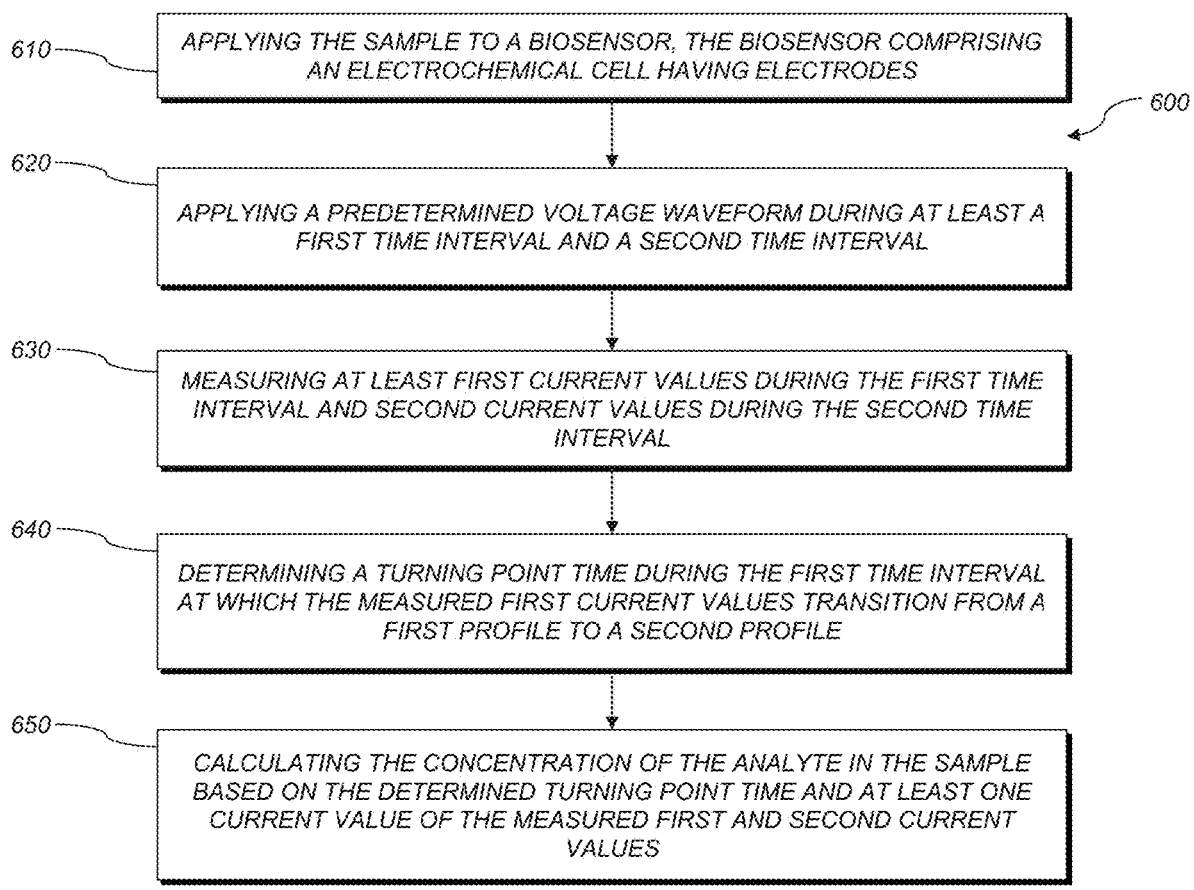
FIGS. 6F & 6G are flowcharts representing methods for determining a concentration of an analyte in a sample in accordance with aspects set forth herein.

FIG. 6F is a flowchart representing a method 600 for determining a concentration of an analyte. In the embodiment of FIG. 6F, the method 600 at block 610 applies the sample to a biosensor. The biosensor may be an electrochemical cell having electrodes, such as test strip 62 of FIG. 1. In one example, the electrodes of the electrochemical cell comprise a bare electrode and an at least partially reagent covered electrode. In another example, the electrodes of the electrochemical cell are one of co-facial or co-planar. In one example, the method further includes driving, after applying the sample to the biosensor, a triggering current between the electrodes of the electrochemical cell, measuring triggering voltage values during driving of the triggering current; and triggering the voltage waveform upon the measured triggering voltage dropping below a predetermined triggering threshold voltage. In another example, the triggering current is between 500-700 nA and the triggering threshold voltage is between 800-1,100 mV.

Next, the method 600 at block 620 applies a voltage waveform during at least a first time interval and a second time interval. For instance, at block 620 any of the waveforms of FIG. 5A, 6D or 6E may be applied to the test strip 62 of FIG. 1. In addition, any waveform may be applied, and may include AC and/or DC components. In a further example, the first predetermined voltage is selected to facilitate oxidation of the interferent from the applied sample.

Continuing, the method 600 at block 630 measures at least first current values during the first time interval and second current values during the second time interval. The waveform could also continue for third, fourth, fifth, etc., time intervals, with measurements of corresponding third, fourth, fifth, etc., current values. In a further example, the measuring of the first and second current values is at a frequency between 50-200 Hz.

The method 600 at block 640 then determines a turning point time during the first time interval at which the measured first current values transition from a first profile to a second profile, for example due to a presence of an interferent in the sample. As explained above, the turning point occurs during the early stages of filling the test strip 62 with the sample. The current value can be measured at the turning point time to determine the turning point current. In one embodiment, the first profile deviates from a Cottrell profile and the second profile essentially follows a Cottrell profile. In another embodiment, an interferent undergoes oxidation at a bare electrode of the electrodes of the electrochemical cell. In a further embodiment, the interferent comprises uric acid or ascorbic acid.

After determining the turning point time at block 640, the method 600 at block 650 calculates the concentration of the analyte in the sample based on the determined turning point time and at least one current value of the measured first and second current values.

For example, the calculating step may be based on the determined turning point time and at least one current value of the measured first current values and at least one current value of the measured second current values. In another embodiment, the calculating step is based on a turning point current value at the turning point time.

In one specific implementation, calculating the analyte concentration includes using an equation of the form $G_{basic}=\Sigma_{i=1}^{m}\Sigma_{j=0}^{m}a_{i,j}x_ix_j+c$, in which:

$G_{basic}$ is the analyte concentration (in mg/dL);

$a_{i,j}$ are coefficients;

$x_0$ is a constant;

$x_1$ is $t_{Turn}$, the turning point time (in seconds);

$x_2$ is $i_r$, a sum of at least some of the measured second current values of the second time interval (in microamperes);

$x_3$ is one of the first current values in the first time interval (in microamperes);

$x_4$ is $i_{Turn}$, a current value at $t_{Turn}$ (in microamperes);

$x_5$ is the inverse of one of the first current values in the first time interval (in 1/microamperes);

$x_6$ is the inverse of one of the first current values in the first time interval (in 1/microamperes); and c is a predetermined constant.

Particular examples of using a linear equation of the form $G_{basic}=\Sigma_{i=1}^{m}\Sigma_{j=0}^{m}a_{i,j}x_ix_j+c$, are set forth below in Table 1.

TABLE 1

Parameters used in linear equation.

| Waveform | $x_1$ | $x_2$ | $x_3$ | $x_4$ | $x_5$ | $x_6$ |
|---|---|---|---|---|---|---|
| FIG. 6D | $t_{Turn}$ | $i_r$ | i(2.2 s) | i(1.1 s) | 1/i(0.05 s) | 1/i(1.0 s) |
| FIG. 6E | $t_{Turn}$ | $i_r$ | i(2.2 s) | 0.00 | $i_{Turn}$ | 1/i(1.0 s) |

In a further specific implementation, calculating the analyte concentration comprises using an equation of the form $G_{basic}=(t_{Turn})^p \cdot (a \cdot |i_{2corr}| - z_{gr})$, in which:

$G_{basic}$ is the analyte concentration (in milligrams per deciliter);

$t_{Turn}$ is the turning point time (in seconds);

$$i_{2corr} = \frac{|i_{pc}| + b|i_{ss}| - c|i_{pb}|}{|i_{pc}| + b|i_{ss}|} \cdot i_r \text{(in microamperes)};$$

$i_{pc}$ is a current close to a negative peak of the third current values in the third time interval (in microamperes);

$i_{pb}$ is a current close to a peak of the second current values in the second time interval (in microamperes);

$i_{ss}$ is a steady state of the third current values in the third time interval;

$i_r$ is a sum of at least some of the measured third current values of the third time interval (in microamperes); and a, b, p and $z_{gr}$ are predetermined coefficients.

Figure 6G:
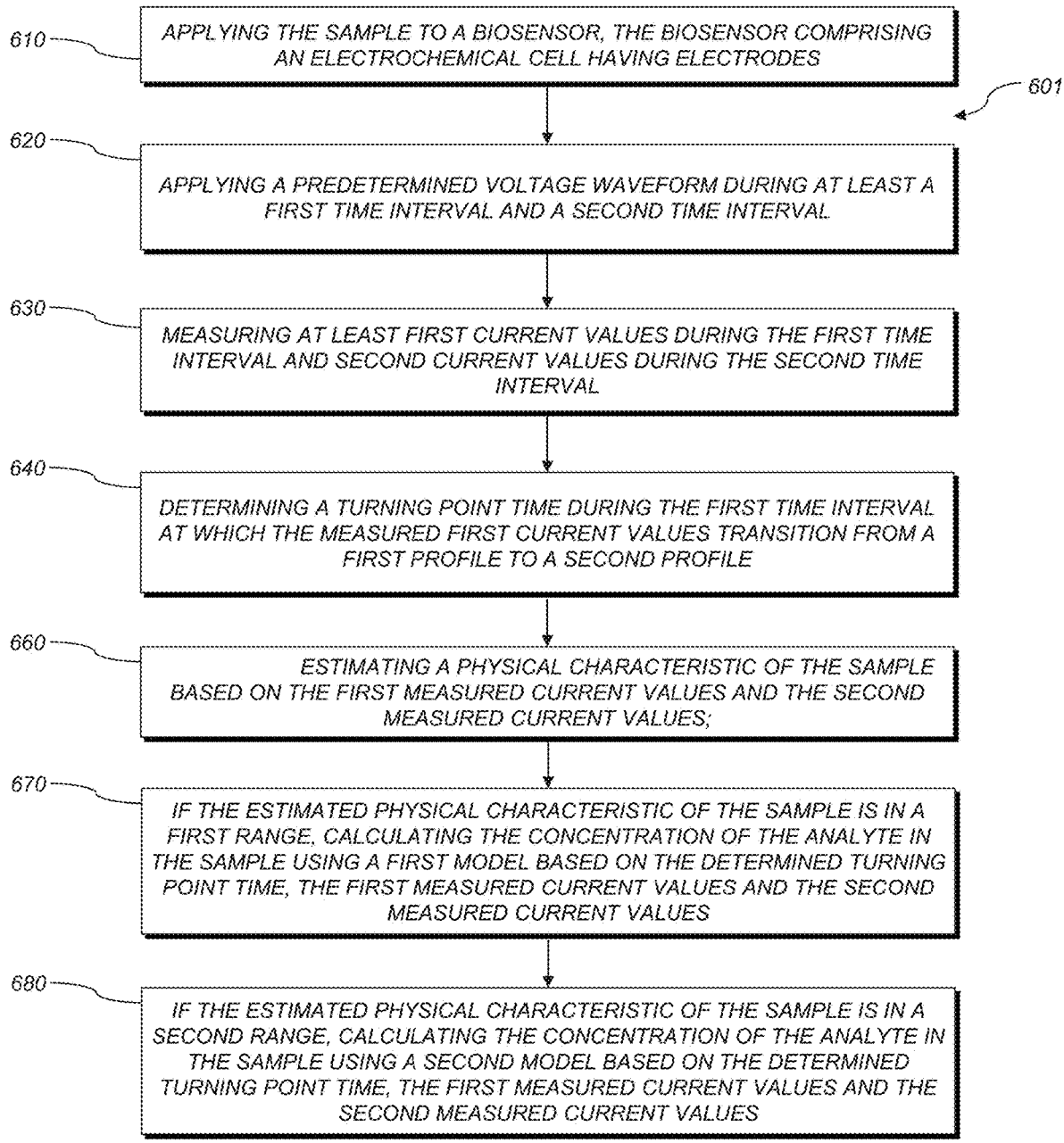

FIG. 6G is a flowchart representing a method 601 for determining a concentration of an analyte. In the embodiment of FIG. 6G, the method 601 at block 610 applies the sample to a biosensor. The biosensor may include an electrochemical cell having electrodes, such as the test strip 62 of FIG. 1.

Next, the method 601 at block 620 applies a voltage waveform during at least a first time interval and a second time interval. For instance, at block 620 any of the waveforms of FIG. 5A, 6D or 6E may be applied to the test strip 62 of FIG. 1

Continuing, the method 601 at block 630 measures at least first current values during the first time interval and second current values during the second time interval.

The method 601 at block 640 then determines a turning point time during the first time interval at which the measured first current values transition from a first profile to a second profile, for example due to a presence of an interferent in the sample.

After determining the turning point time at block 640, the method 601 at block 660 estimates a physical characteristic of the sample based on, for example, one or more of the turning point time, the first measured current values and the second measured current values.

In one case, if the estimated physical characteristic of the sample is in a first range, the method 601 at block 670 calculates the concentration of the analyte in the sample using a first model, the first measured current values and the second measured current values. If the estimated physical characteristic of the sample is in a second range, the method 601 at block 670 calculates the concentration of the analyte in the sample using a second model based on the determined turning point time, the first measured current values and the second measured current values.

In one specific example, calculating the analyte concentration using the first model comprises using an equation of the form $G_{basic}^{1}=\Sigma_{i=1}^{m}\Sigma_{j=0}^{m}a_{i,j}^{1}x_i^{1}x_j^{1}+c_1$, and calculating the analyte concentration using the second model comprises using an equation of the form:

$$G_{basic}^{2}=\Sigma_{i=1}^{m}\Sigma_{j=0}^{m}a_{i,j}^{2}x_i^{2}x_j^{2}+c_2, \text{ in which:}$$

$G_{basic}^{1}$ is the analyte concentration calculated using the first model (in mg/dL);

$a_{i,j}^{1}$ are first model predetermined coefficients;

$x_0^{1,2}$ are constants (e.g., equal to 1);

$x_i^{1}$ are first model predictors based on the measured current values;

$c_1$ is a first model predetermined constant;

$G_{basic}^{2}$ is the analyte concentration calculated using the second model (in mg/dL);

$a_{i,j}^{2}$ are second model predetermined coefficients;

$x_i^{2}$ are second model predictors based on the measured current values; and $c_2$ is a second model predetermined constant.

In one embodiment, the first model comprises first coefficients and the second model comprises second coefficients, and the first coefficients and the second coefficients are determined by linear optimization. In another embodiment, estimating the physical characteristic comprises using the turning point time.

Set forth below is a working example of estimating one particular physical characteristic, namely the hematocrit level, using either of the two waveforms of FIG. 6D or FIG. 6E.

The first step is that a linear model is used to estimate the hematocrit H. The model uses the following equation: $H=\Sigma_{i=1}^{m}\Sigma_{j=0}^{m}a_{i,j}^{H}x_i^{H}x_j^{H}+c_H$, in which the linear model estimators and coefficients are given by Tables 2-6 below, depending on which waveform is selected from Table 1.

TABLE 2

Linear Model Estimators for Hematocrit

| | FIG. 6D waveform | FIG. 6E waveform |
|---|---|---|
| $x_1^H$ | ln(tTurn) | ln(tTurn) |
| $x_2^H$ | ln(i1.0) | ln(i1.0) |
| $x_3^H$ | ln(i0.05) | ln(i0.05) |
| $x_4^H$ | i2.2 | i2.2 |
| $x_5^H$ | i1.1 | iTurn |
| $x_6^H$ | ln($i_r$) | ln($i_r$) |

TABLE 3

Coefficients for FIG. 6D waveform

| Term | coefficient | Term | coefficient |
|---|---|---|---|
| C | 187 | 'x2:x5' | 0.313 |
| 'x1' | −1.47 | 'x2:x6' | −4.17 |
| 'x2' | 35.3 | 'x3:x5' | 0.254 |
| 'x3' | −21.7 | 'x3:x6' | 1.45 |
| 'x4' | 4.23 | 'x4:x5' | −0.0938 |
| 'x5' | −3.09 | 'x4:x6' | −1.45 |
| 'x6' | −49.4 | 'x5:x6' | 0.532 |
| 'x1:x2' | 3.65 | 'x1^2' | −7.8 |
| 'x1:x3' | −1.48 | 'x2^2' | 1.87 |
| 'x1:x4' | −0.311 | 'x3^2' | −2.71 |
| 'x1:x5' | −0.194 | 'x4^2' | 0.213 |
| 'x1:x6' | −3.47 | 'x5^2' | 0.0436 |
| 'x2:x3' | 2.76 | 'x6^2' | 4.08 |
| 'x2:x4' | 0.89 | | |

TABLE 4

Coefficients for FIG. 6E waveform

| Term | coefficient | Term | coefficient |
|---|---|---|---|
| C | 126 | 'x2:x6' | −7.1 |
| 'x1' | 4.2 | 'x3:x4' | −0.644 |
| 'x2' | 36.4 | 'x3:x5' | −0.97 |
| 'x3' | −51.7 | 'x3:x6' | 3.08 |
| 'x4' | −2.64 | 'x4:x5' | −0.0703 |
| 'x5' | −3.16 | 'x4:x6' | −0.89 |
| 'x6' | −32.9 | 'x5:x6' | 0.193 |
| 'x1:x2' | −3.17 | 'x1^2' | −6.82 |
| 'x1:x3' | −2.95 | 'x2^2' | 5.75 |
| 'x1:x4' | −1.28 | 'x3^2' | −7.53 |
| 'x1:x6' | −3.86 | 'x4^2' | 0.252 |
| 'x2:x3' | −3.36 | 'x5^2' | −0.0278 |
| 'x2:x4' | 1.98 | 'x6^2' | 2.84 |
| 'x2:x5' | −0.613 | | |

Next, after using the equation set forth above to determine the estimated hematocrit H, the linear model glucose calculation is used with the following coefficients selected dependent upon which range H falls into, depending on which waveform was selected:

TABLE 5

Coefficients for waveform of FIG. 6D

| Hct ≥0 & <25% | coefficient | Hct ≥25 & <35% | coefficient | Hct ≥35 & <45% | coefficient |
|---|---|---|---|---|---|
| C | −2.86 | C | −7.14 | C | −14.5 |
| 'x1' | −2.95 | 'x1' | −2.91 | 'x1' | −2 |
| 'x2' | −14.8 | 'x2' | −32.8 | 'x2' | −7.4 |
| 'x3' | 1.12 | 'x3' | 2.21 | 'x3' | 0.721 |
| 'x4' | −2.12 | 'x4' | 0.019 | 'x4' | −3.14 |
| 'x5' | −1.63 | 'x5' | −3.15 | 'x5' | −1.1 |

TABLE 5-continued

Coefficients for waveform of FIG. 6D

| Hct ≥0 & <25% | coefficient | Hct ≥25 & <35% | coefficient | Hct ≥35 & <45% | coefficient |
|---|---|---|---|---|---|
| 'x1:x2' | 0.06 | 'x1:x2' | 5.31 | 'x1:x2' | 4 |
| 'x1:x4' | −0.914 | 'x1:x3' | −0.316 | 'x1:x3' | −0.234 |
| 'x1:x5' | 0.267 | 'x1:x4' | −1.21 | 'x1:x4' | −1.57 |
| 'x2:x4' | −1.29 | 'x1:x5' | 0.574 | 'x1:x5' | 0.453 |
| 'x2:x5' | 1.2 | 'x2:x4' | −1.16 | 'x2:x4' | −8.07 |
| 'x3:x4' | 0.065 | 'x2:x5' | 1.3 | 'x2:x5' | 2.9 |
| 'x3:x5' | −0.0691 | 'x3:x4' | 0.0527 | 'x3:x4' | 0.459 |
| 'x4:x5' | −0.296 | 'x3:x5' | −0.0736 | 'x3:x5' | −0.167 |
| 'x1^2' | 0.422 | 'x4:x5' | −0.314 | 'x4:x5' | −1.11 |
| 'x3^2' | 8.66E−05 | 'x1^2' | 0.526 | 'x1^2' | 0.597 |
| 'x4^2' | 0.602 | 'x3^2' | 0.000101 | 'x2^2' | 0.145 |
| 'x5^2' | 0.0762 | 'x4^2' | 0.65 | 'x3^2' | −0.00041 |
| | | 'x5^2' | 0.0782 | 'x4^2' | 1.69 |
| | | | | 'x5^2' | 0.206 |

| Hct ≥45 & >55% | coefficient | Hct ≥55 | coefficient |
|---|---|---|---|
| C | −14.1 | C | −18.7 |
| 'x1' | −6 | 'x1' | −15.6 |
| 'x2' | −3.97 | 'x2' | −16.6 |
| 'x3' | 0.559 | 'x3' | 1.32 |
| 'x4' | −9.76 | 'x4' | 7.25 |
| 'x5' | 0.358 | 'x5' | −4.8 |
| 'x1:x2' | 8.95 | 'x1:x2' | 15.4 |
| 'x1:x3' | −0.513 | 'x1:x3' | −0.846 |
| 'x1:x4' | −5.38 | 'x1:x4' | −22.4 |
| 'x1:x5' | 1.49 | 'x1:x5' | 5.08 |
| 'x2:x4' | 13.7 | 'x2:x4' | −10.5 |
| 'x2:x5' | −3.17 | 'x2:x5' | 2.52 |
| 'x3:x4' | −0.828 | 'x3:x4' | 0.537 |
| 'x3:x5' | 0.188 | 'x3:x5' | −0.131 |
| 'x4:x5' | 0.676 | 'x4:x5' | −4.77 |
| 'x1^2' | 1.47 | 'x1^2' | 4.6 |
| 'x2^2' | −0.675 | 'x3^2' | 0.000147 |
| 'x3^2' | 0.00244 | 'x4^2' | 11.1 |
| 'x4^2' | 0.907 | 'x5^2' | 0.519 |
| 'x5^2' | −0.22 | | |

TABLE 6

Coefficients for waveform of FIG. 6E

| Hct ≥0 & <25% | coefficient | Hct ≥25 & <35% | coefficient | Hct ≥35 & <45% | coefficient |
|---|---|---|---|---|---|
| C | −8.05 | C | −12.5 | C | −10.8 |
| 'x1' | 1.99 | 'x1' | −5.55 | 'x1' | −23.1 |
| 'x2' | −1.74 | 'x2' | −5.24 | 'x2' | 3 |
| 'x3' | 0.323 | 'x3' | 0.589 | 'x3' | 0.123 |
| 'x4' | −1.37 | 'x4' | −7.73 | 'x4' | −11.1 |
| 'x5' | −5.07 | 'x5' | 6.26 | 'x5' | 24.4 |
| 'x1:x2' | −9.96 | 'x1:x2' | −36.5 | 'x1:x2' | −64.7 |
| 'x1:x3' | 0.619 | 'x1:x3' | 2.12 | 'x1:x3' | 3.99 |
| 'x1:x4' | −2.69 | 'x1:x4' | 21.2 | 'x1:x4' | −10.6 |
| 'x1:x5' | 0.669 | 'x1:x5' | −61 | 'x1:x5' | 0.721 |
| 'x2:x4' | −2 | 'x2:x4' | −5.59 | 'x2:x3' | 0.029 |
| 'x2:x5' | 12.2 | 'x2:x5' | 42.3 | 'x2:x4' | −11.2 |
| 'x3:x4' | 0.112 | 'x3:x4' | 0.316 | 'x2:x5' | 73.8 |
| 'x3:x5' | −0.747 | 'x3:x5' | −2.46 | 'x3:x4' | 0.652 |
| 'x4:x5' | 1.65 | 'x4:x5' | −24.2 | 'x3:x5' | −4.53 |
| 'x2^2' | −0.0638 | 'x1^2' | 19.9 | 'x4:x5' | 9.53 |
| 'x3^2' | 0.000307 | 'x3^2' | 0.000091 | 'x2^2' | −0.0795 |
| 'x4^2' | 0.364 | 'x4^2' | 2.06 | 'x3^2' | −0.00135 |
| | | 'x5^2' | 42.3 | 'x4^2' | 1.11 |
| | | | | 'x5^2' | −0.421 |

| Hct ≥45 & <55% | coefficient | Hct ≥55 | coefficient |
|---|---|---|---|
| C | −13.2 | C | −25.1 |
| 'x1' | −55.6 | 'x1' | −29.7 |
| 'x2' | −8.37 | 'x2' | −4.01 |
| 'x3' | 0.831 | 'x3' | 0.624 |
| 'x4' | −14.6 | 'x4' | −4.34 |

TABLE 6-continued

| Coefficients for waveform of FIG. 6E | | | |
|---|---|---|---|
| 'x5' | 56.2 | 'x5' | 19.5 |
| 'x1:x2' | 21 | 'x1:x2' | 11.6 |
| 'x1:x3' | −0.962 | 'x1:x3' | −0.398 |
| 'x1:x5' | −2.2 | 'x1:x4' | −68.4 |
| 'x2:x3' | −0.043 | 'x1:x5' | 169 |
| 'x2:x4' | 4.43 | 'x2:x3' | −0.344 |
| 'x2:x5' | −22.3 | 'x2:x4' | −9.47 |
| 'x3:x4' | −0.311 | 'x2:x5' | −4.28 |
| 'x3:x5' | 1.06 | 'x3:x4' | 0.501 |
| 'x4:x5' | −3.18 | 'x4:x5' | 69.3 |
| 'x1^2' | −0.998 | 'x1^2' | −60.4 |
| 'x2^2' | 0.212 | 'x2^2' | 3.01 |
| 'x3^2' | 0.00197 | 'x3^2' | 0.01 |
| 'x4^2' | 4.9 | 'x4^2' | 1.46 |
| 'x5^2' | 3.27 | 'x5^2' | −110 |

Figure 6H:
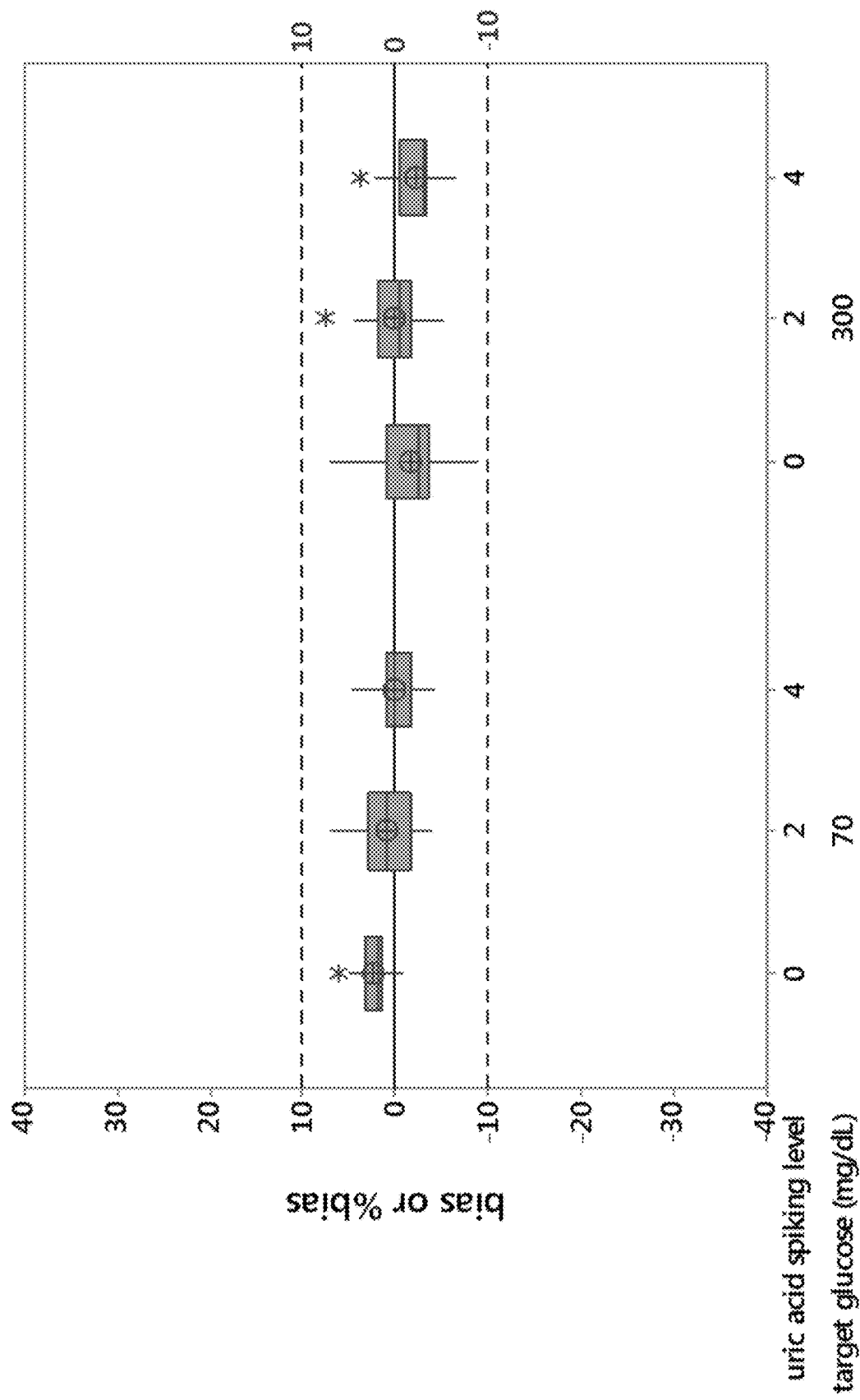
FIG. 6H depicts experimental validation of improved analyte concentration measurement in the presence of an interferent in accordance with aspects set forth herein.

FIG. 6H depicts experimental validation of improved analyte concentration measurement in the presence of an interferent using the linear model of Table 1 with the waveform of FIG. 6D. In FIG. 6H, from the left side, the first three boxplots depict the target glucose concentration of sample blood of 70 mg/dL when the amount of uric acid is at spiking levels 0, 2 and 4, respectively. The second three boxplots depict the target glucose concentration of sample blood of 300 mg/dL when the amount of uric acid is at spiking levels 0, 2 and 4, respectively, as defined in Table 7 below. Each individual boxplot comprises all results at spiking levels 0, 2 and 4 of ascorbic acid, as defined in Table 7.

TABLE 7

| Definition of Spiking Levels Depicted in FIG. 6H. | | | |
|---|---|---|---|
|  | Level 0 | Level 2 | Level 4 |
| Added uric acid (mg/dL) | 0.00 | 11.91 | 23.81 |
| Added ascorbic acid (mg/dL) | 0.00 | 3.19 | 6.38 |

As depicted in FIG. 6H, using the linear model of Table 4 and 7, as described above, the present technique provides corrected analyte concentration measurements.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

To the extent that the claims recite the phrase "at least one of" in reference to a plurality of elements, this is intended to mean at least one or more of the listed elements, and is not limited to at least one of each element. For example, "at least one of an element A, element B, and element C," is intended to indicate element A alone, or element B alone, or element C alone, or any combination thereof "At least one of element A, element B, and element C" is not intended to be limited to at least one of an element A, at least one of an element B, and at least one of an element C.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description set forth herein has been presented for purposes of illustration and description, but is not intended to be exhaustive or limited to the form disclosed. Many modifications and variations will be apparent to those of ordinary skill in the art without departing from the scope and spirit of the disclosure. The embodiment was chosen and described in order to best explain the principles of one or more aspects set forth herein and the practical application, and to enable others of ordinary skill in the art to understand one or more aspects as described herein for various embodiments with various modifications as are suited to the particular use contemplated.

The invention claimed is:

1. A method for determining a concentration of an analyte in a fluidic sample, the method comprising:
   applying the fluidic sample to a biosensor, the biosensor comprising an electrochemical cell having electrodes;
   applying a voltage waveform comprising at least a first predetermined voltage applied during a first time interval and a second predetermined voltage different from the first predetermined voltage applied during a second time interval;
   measuring at least first current values during the first time interval and second current values during the second time interval;
   determining a turning point time during the first time interval at which the measured first current values transition from a first profile to a second profile; and estimating a physical characteristic of the sample based on the turning point time, the first measured current values and the second measured current values;

if the estimated physical characteristic of the sample is in a first range, calculating the concentration of the analyte in the sample using a first model based on the first measured current values and the second measured current values; and if the estimated physical characteristic of the sample is in a second range, calculating the concentration of the analyte in the sample using a second model based on the determined turning point time, the first measured current values and second measured current values.

2. The method of claim 1, wherein the first model comprises first coefficients and the second model comprises second coefficients, and the first coefficients and the second coefficients are determined by linear optimization.

3. The method of claim 1, wherein the physical characteristic is the hematocrit level of the fluidic sample.

4. The method of claim 2, wherein the voltage waveform further comprises a third predetermined voltage applied during a third time interval, the method further comprising measuring third current values during the third time interval.

5. The method of claim 4, wherein calculating the analyte concentration using the first model comprises using an equation of the form $G_{basic}^1=(a^1 \cdot |i_{2corr}|-z_{gr}^1)$, and calculating the analyte concentration using the second model comprises using an equation of the form:

$G_{basic}^2=(a^2 \cdot |i_{2corr}|-z_{gr}^2)$, in which:

$G_{basic}^1$ is the analyte concentration calculated using the first model (in mg/dL);

$a^1$ and $z_{gr}^1$ are first model predetermined coefficients;

$G_{basic}^2$ is the analyte concentration calculated using the second model (in mg/dL);

$a^2$ and $z_{gr}^2$ are second model predetermined coefficients;

$$i_{2corr} = \frac{|i_{pc}|+b|i_{ss}|-c|i_{pb}|}{|i_{pc}|+b|i_{ss}|} \cdot i_r \text{(in microamperes);}$$

$i_{pc}$ is close to a negative peak of the third current values in the third time interval (in microamperes);

$i_{pb}$ is close to a peak of the second current values in the second time interval (in microamperes);

$i_{ss}$ is a steady state of the third current values in the third time interval;

$i_r$ is a sum of at least some of the measured third current values of the third time interval (in microamperes); and b, c and p are predetermined coefficients.

6. The method of claim 1, wherein the biosensor comprising the electrochemical cell has at least two electrodes.

7. The method of claim 6, wherein the at least two electrodes of the electrochemical cell are disposed either cofacially or coplanar relative to one another.

8. The method of claim 7, wherein the at least two electrodes of the electrochemical cell comprise a bare electrode and an at least partially reagent covered electrode.

9. The method of claim 1, wherein the measuring of the first and second current values is at a frequency between 50-200 Hz.

10. The method of claim 1, wherein the measured first current values transition from the first profile to the second profile due to the presence of an interferent in the sample.

11. The method of claim 10, wherein a current $i_{pb}$ representative of a transition from a first predetermined voltage of the waveform during the first time interval and a second predetermined voltage of the waveform during the second time interval occurs during an initial portion of the second time interval.

12. The method of claim 11, wherein the turning point time occurs prior to the occurrence of $i_{pb}$.

13. The method of claim 10, wherein the interferent comprises uric acid or ascorbic acid.

14. The method of claim 1, wherein the first profile deviates from a Cottrell profile and the second profile follows a Cottrell profile.

* * * * *